US007413732B1

(12) United States Patent
Possee et al.

(10) Patent No.: US 7,413,732 B1
(45) Date of Patent: Aug. 19, 2008

(54) BACULOVIRUS EXPRESSION SYSTEM

(75) Inventors: Robert David Possee, Witney (GB); Linda Anne King, Witney (GB)

(73) Assignees: Oxford Brookes University (GB); Natural Environment Research Council (GB)

( * ) Notice: Subject to any disclaimer, the term of this patent is extended or adjusted under 35 U.S.C. 154(b) by 0 days.

(21) Appl. No.: 09/807,809

(22) PCT Filed: Aug. 14, 2000

(86) PCT No.: PCT/GB00/03144

§ 371 (c)(1),
(2), (4) Date: Jul. 30, 2001

(87) PCT Pub. No.: WO01/12829

PCT Pub. Date: Feb. 22, 2001

(30) Foreign Application Priority Data

Aug. 18, 1999 (GB) ................................. 9919409.4

(51) Int. Cl.
*A01N 63/00* (2006.01)
*C12N 15/64* (2006.01)
*C12N 5/10* (2006.01)
*C12N 15/74* (2006.01)
*C12N 15/00* (2006.01)

(52) U.S. Cl. ..................... 424/93.1; 435/91.4; 435/348; 435/477; 435/440; 435/320.1; 435/69.1

(58) Field of Classification Search .............. 435/172.3, 435/235.1, 320.1, 6, 348, 325, 69.1, 70.1, 435/170, 455, 456, 477, 483, 71.1; 536/23.72
See application file for complete search history.

(56) References Cited

U.S. PATENT DOCUMENTS

| | | | | |
|---|---|---|---|---|
| 5,348,886 | A * | 9/1994 | Lee et al. .................... | 435/69.1 |
| 5,750,383 | A * | 5/1998 | Blissard et al. ............. | 435/457 |
| 6,225,060 | B1 * | 5/2001 | Clark et al. .................... | 435/6 |
| 6,911,206 | B1 * | 6/2005 | Campos et al. .......... | 424/192.1 |

FOREIGN PATENT DOCUMENTS

| | | |
|---|---|---|
| EP | 0 536 646 A2 | 10/1992 |
| WO | WO 95/09923 | 4/1995 |
| WO | WO 97 43403 A2 | 11/1997 |
| WO | WO 98 22607 A2 | 5/1998 |
| WO | WO 99 10515 A2 | 3/1999 |

OTHER PUBLICATIONS

Merrington et al, An Autographa californica nucleopolyhedrovirus lef-2 mutant: consequences for DNA replication and very late gene expression, Virology, 1996, vol. 217, pp. 338-348.*
Kool et al, Identification of genes involved in DNA replication of the Autographa californica baculovirus, 1994, PNAS, vol. 91, pp. 11212-11216.*
Nasmyth et al. A new method for the isolation of recombinant baculovirus. Nucleic Acid Research, 1992 vol. 20 (1) pp. 97-104.*
Gomi, S. et al., (1997) "Deletion analysis of four of eighteen late gene expression factor gene homologues of the baculovirus BmNPV", *Virology* 230, 35-47.
Merrington, C. L. et al., (1996) "An *Autographa californica* nucleopolyhedrovirus lef-2 mutant: Consequences for DNA replication and very late gene expression", *Virology* 217, 338-348.
Patel, D. et al., (1992) "A new method for the isolation of recombinant baculovirus", *Nucleic Acids Res.* 20, 97-104.
Shikata, M. et al., (1998) "Isolation and characterization of a temperature-sensitive mutant of Bombyx mori nucleopolyhedrovirus for a putative RNA polymerase gene", *Journ. of Gen'l Virology* 79, 2071-2078.
Ahrens, C. H. & Rohrmann, G. F. (1995) "Identification of essential trans-acting regions required for DNA replication of the *Orgyia pseudotsugata* baculovirus multinucleocapsid nuclear polyhedrosis virus: *lef-1* is an essential replication gene", *Virology* 207, 417-428.
Ayres, M. D. et al., (1994) "The complete DNA sequence of *Autographa californica* nuclear polyhedrosis virus", *Virology* 202, 586-605.
Blissard, G. W. et al., (1989) "Location, sequence, transcriptional mapping, and temporal expression of the *gp64* envelope glycoprotein gene of the *Orgyia pseudotsugata* multicapsid nuclear polyhedrosis virus", *Virology* 170, 537-555.
Durantel, D. et al., (1998a) "The *pnk/pnl* gene (ORF 86) of *Autographa californica* nucleopolyhedrovirus is a non essential, immediate early gene", *J. Gen. Virol.* 79, 629-637.
Durantel, D. et al., (1998b) "Temporal expression of the *AcMNPV lef-4* gene and subcellular localization of the protein", *Virology* 241, 276-284.
Eckner, R. et al., (1994) "Molecular cloning and functional analysis of the adenovirus E1A-associated 300-kD protein (p300) reveals a protein with properties of a transcriptional adaptor", *Genes Dev.* 8, 869-884. Abstract only.
Evan, G. I. et al., (1986) "Characterization of the human c-myc protein using antibodies prepared synthetic peptides", *Ciba Found Symp.* 119, 245-263. Abstract only.
Evans, J. T. et al., (1997) "Characterisation of the interaction between the baculovirus replication factors LEF-1 and LEF-2," *J. Virol.* 71, 3114-3119.
Fan, X. et al., (1998) "Identification and characterization of a protein kinase-interacting protein encoded by the *Autographa californica* Nuclear polyhedrosis virus", *Virology* 240, 175-182.

(Continued)

*Primary Examiner*—Maria B Marvich
(74) *Attorney, Agent, or Firm*—Kilpatrick Stockton LLP

(57) ABSTRACT

The application relates for method for cloning the gene comprising the steps of: 1. Providing a replication-deficient baculovirus vector, 2. Providing a rescue vector comprising (a) nucleic acid sequence which is capable of restoring replication in the replication-deficient baculovirus vector and (b) at least one gene to be cloned; 3. Causing the replication-deficient baculovirus vector and rescue vector to recombine to produce a replication-enabled baculovirus vector comprising the at least one gene to be cloned; and 4. Growing the replication-enabled baculovirus vector within a suitable invertebrate cell, such as an insect cell. Preferably the baculovirus vector is based upon AcMNPV. Also disclosed are replication-deficient baculovirus vectors, rescue vectors, cells containing such vectors and kits comprising such vectors.

4 Claims, 7 Drawing Sheets

OTHER PUBLICATIONS

Figure 1:
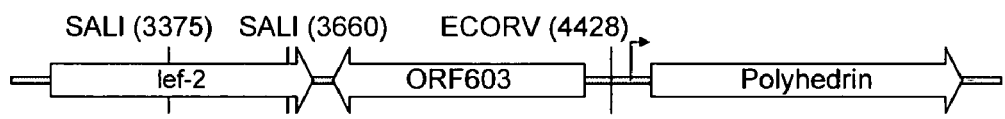
Figure 1:
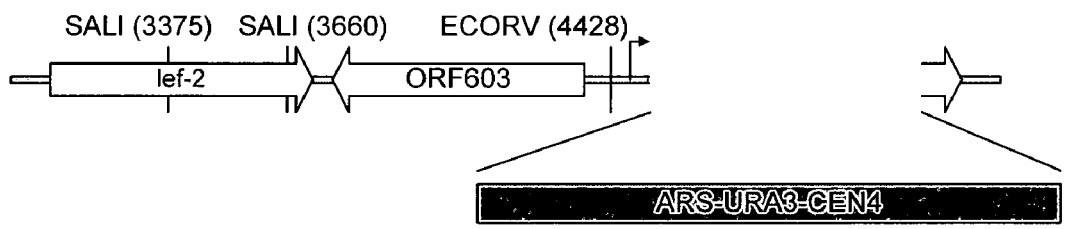
Figure 1:
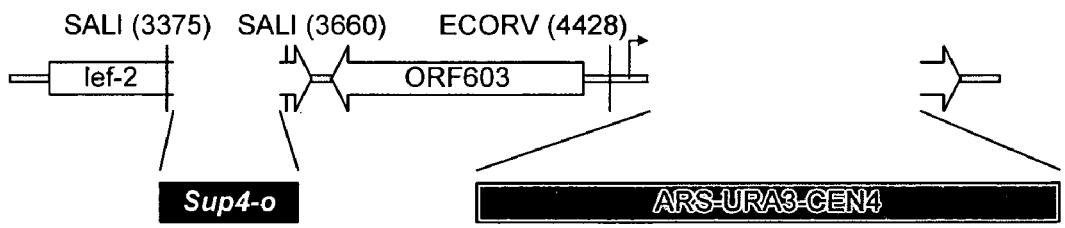

Fan, X. et al., (1996) "Temperature-sensitive mutations in the protein kinase-1 (*pk-1*) gene of the *Autographa californica* nuclear polyhedrosis virus that block very late gene expression", *Virology* 224, 1-9.

Fitzgerald-Hayes, M. (1987) "Yeast centromeres", *Yeast* 3, 187-200. Abstract only.

Funk, C.J. et al., (1998) "Differential stability of baculovirus late transcription complexes during initiation and elongation", *Virology* 241, 131-140.

Goodman, H. M. et al., (1997) "Nucleotide sequence of a mutant eukaryotic gene: the yeast tyrosine-inserting ochre suppressor *sup4-0*", *Proc. Natl. Acad. Sci. U.S.A.* 74, 5453-5457. Abstract only.

Graham, F. L. et al., (1973) "A New Technique for the Assay of Infectivity of Human Adenovirus 5 DNA", *Virol.* 52, 456-467.

Guarino, L. A. et al., (1998) "A virus-encoded RNA polymerase purified from baculovirus infected cells", *J. Virol.* 72, 7985-7991.

Hawtin, R. E. et al., (1995) "Identification and preliminary characterization of a chitinase gene in the *Autographa californica* nuclear polyhedrosis virus genome", *Virology* 212, 673-685.

Ito, H. et al., (1983) "Transformation of intact yeast cells treated with alkali cations", *J. Bacteriol.* 153, 163-168. Abstract only.

King, L. A. & Possee, R. D. (1992) "The Baculovirus Expression System. A Laboratory Guide", first ed. Chapman and Hall, London.

Kitts, P. A. & Possee, R.D. (1993) "A Method for producing recombinant baculovirusexpression vectors at high frequency", *BioTechniques* 14, 810-817.

Kool, M., et al., (1994) "Identification of genes involved in DNA replication of the *Autographa californica* baculovirus", *Proc. Natl. Acad. Sci. U.S.A.* 91, 11212-11216.

Kool, M., et al., (1995) "Replication of baculovirus DNA", *J. Gen. Virol.* 76, 2103-2118.

Laemmli, U. K. (1970) "Cleavage of structural proteins during the assembly of the head bacteriophage T4", *Nature* 227, 680-685.

Lu, A. et al., (1997) "Baculovirus DNA replication", In: *The baculoviruses* (Miller, L.K., ed.) p. 171-192. Plenum press, New York.

Lu, A. et al., (1995) "The role of eighteen baculovirus late expression factor genes in transcription and DNA replication", *J. Virol.* 69, 975-982.

Lu, A. et al., (1994), "Identification of three late expression factor genes within the 33.8- to 43.3-map unit region of *Autographa californica* nuclear polyhedrosis virus", *J. Virol.* 68, 6710-6718.

Lu, A. et al., (1997)"Regulation of baculovirus late and very late gene expression", *The baculoviruses* (Miller, L. K., ed.) p. 193-216. Plenum press, New York.

Luckow, V. A. et al., (1993) "Efficient generation of infectious recombinant baculoviruses by site-specific transposon-mediated insertion of foreign genes into a baculovirus genome propagated in *Escherichia coli*", *J. Virol.* 67 , 4566-4579.

McLachlin, J. R. et al., (1998) "A baculovirus mutant defective in PKIP, a protein which interacts with a virus-encoded protein kinase", *Virology* 246, 379-391.

McLachlin, J.R. et al., (1994) "Identification and characterization of *vlf-1*, a baculovirus gene involved in very late gene expression", *J. Virol.* 68, 7746-7756.

Newman, A. et al., (1991) "Mutations in yeast U5 snRNA alter the specificity of 5' splice-site cleavage", *Cell* 65, 115-123.

Passarelli, A. L. et al., (1993a) "Three baculovirus genes involved in late and very late gene expression: *ie-1, ie-N,* and *lef-2*", *J. Virol.* 67, 2149-2158.

Possee, R. D. (1986) "Cell-surface expression of influenza virus haemagglutinin in insect cells using a baculovirus vector", *Virus Research* 5, 43-59.

Possee, R. D. et al., (1990) "Nucleotide sequence of the *Autographa californica* Nuclear Polyhedrosis Virus 9.4 Kbp EcoRI-I and R (Polyhedrin Gene Region)", *Virology*, 185, 229-241 (Submitted manuscript included).

Proudfoot, N. (1991) "Poly(A) signals", *Cell* 64, 671-674.

Rapp, J. C. et al., (1998) "Nineteen baculovirus open reading frames, including lef-12 support late gene expression", *J. Virol.* 72, 10197-10206.

Ross, L. & Guarino, L. A. (1997) "Cycloheximide inhibition of delayed early gene expression in baculovirus-infected cells", *Virology* 232, 105-113.

Sambrook, J. et al., (1989) "Molecular Cloning: A Laboratory Manual", Cold Spring Harbor Laboratory, Cold Spring Harbor, NY.

Schiestl, R. H. & Gietz, R. D. (1989) "High efficiency transformation of intact yeast cells using single stranded nucleic acids as a carrier", *Curr. Genet.* 16, 339-346. Abstract only.

Sherman, F (1991) "Getting started with yeast", *Methods in Enzymol.* 194, 3-21.

Shizuya, H. et al., (1992) "Cloning and stable maintenance of 300-kilobase pair fragments of human DNA in *Escherichia coli* using an F-factor-based vector", *Proc. Natl. Acad. Sci* USA 89, 8794-8797.

Stinchcomb, D. T. et al., (1979) "Isolation and characterisation of a yeast chromosomal replicator", *Nature* 282, 39-43.

Todd, J. W. et al., (1995) "Eighteen baculovirus genes, including *lef-11, p35, 39k,* and *p47,* support late gene expression", *J. Virol.* 69, 968-974.

Todd, J. W. et al., (1996) "Factors regulating baculovirus late and very late gene expression in transient-expression assays", *J. Virol.* 70, 2307-2317.

Vialard, J. E. and Richardson, C. D. (1993) "The 1629-nucleotide open reading frame located downstream of the *Autographa californica* nuclear polyhedrosis virus polyhedrin gene encodes a nucleocapsid-associated phosphoprotein", *J. Virol.* 67, 5859-5866.

Weyer, U. and Possee, R.D. (1988) "Functional analysis of the p10 gene 5' leader sequence of the *Autographa californica* nuclear polyhedrosis virus", *Nucleic Acids Research* 16, 3635-3653.

Weyer, U. et al., (1990) "Analysis of very late gene expression by *Autographa californica* nuclear polyhedrosis virus and the further development of multiple expression vectors", *Journal of General Virology* 71, 1525-1534.

Wigler, M. et al., (1977) "Transfer of Purified Herpes Virus Thymidine Kinase Gene to Cultured Mouse Cells", *Cell* 11, 223-232.

Yang, S. & Miller, L. K. (1998) "Expression and mutational analysis of the baculovirus very late factor 1 (*vlf-1*) gene", *Virology* 245, 99-109.

Yang, S. & Miller, L. K. (1998b) "Control of baculovirus polyhedrin gene expression by very late factor 1", *Virology* 248, 131-138.

\* cited by examiner (a) AcMNPV (b) AcAUC (b) AcΔlef-2.*sup4-o*

BACULOVIRUS EXPRESSION SYSTEM

The invention relates to a method for cloning a gene, to replication deficient baculovirus vectors and rescue vectors for use in the method, to cells comprising such vectors and to kits comprising such vectors.

Baculoviruses have been isolated from a number of invertebrates. Most examples have been found in insect species, but there are some reports of baculoviruses, which are pathogenic for crustacea. Baculovirus infections have been described in over 600 species of insects including *Lepidoptera, Hymenoptera, Diptera* and *Coleoptera*. Baculoviruses and their use as expression vectors are discussed in the book by King, L. A and Possee, R. D. "The Baculovirus Expression System. A Laboratory Guide" (Chapman and Hall, 1992).

Baculoviruses have a large, double stranded covalently closed circular DNA genome of between 88 and 180 kilobase pairs (kbp). This associates with a highly basic (arginine-rich) protein of 6.5 kiloDaltons (kDa), within a rod-shaped nucleocapsid, which contains a 39 kDa capsid protein. Other structural components almost certainly remain to be identified. The size of the virus genome determines the length of the nucleocapsid, which may be 200-400 nm.

The nucleocapsids are further packaged within a lipoprotein envelope to form a virus particle or virion. These structures may be occluded within a crystalline matrix or polyhedron consisting largely of a single protein (polyhedrin) of about 30 kDa, and form in the nucleus of infected cells. Polyhedra are large structures ranging in size from 1-15 μM in diameter and with an outer polysaccharide envelope, which appears to confer additional strength and protection.

Baculoviruses are usually named after the host from which they are isolated. For example, the baculovirus isolated from alfalfa looper was designated *Autographa californica* (Ac) MNPV. However, baculoviruses which are almost identical to AcMNPV have been found in *Trichoplusia ni, Galleria mellonella* and *Rachiplusia ou*. The AcMNPV has been extensively studied at the molecular level largely because of its efficient replication in cell culture. In consequence, it was a logical example to be exploited as an expression vector. Cells derived from *Spodoptera frugiperda* or *Trichoplusia ni* are normally used as the host for propagating the virus. It should be mentioned, however, that other baculovirus expression vectors are known, for example from *Bombyx mori* (silkworm) (Bm) NPV. This latter system, while particularly useful for producing recombinant proteins in silkworm larvae, which are easily reared and handled, has not achieved such widespread popularity as the AcMNPV system.

Baculoviruses are used as expression vectors by inserting genes from other species (e.g. humans, other vertebrates, plants, bacteria and viruses) into the virus genome. They are positioned under the control of a very strong baculovirus gene promoter (eg. polyhedrin) to make a recombinant virus. This promoter drives expression of the foreign gene to make messenger RNA, which in turn makes protein in the recombinant virus-infected cell. The advantage of using this system is that the level of protein generated in the virus-infected cells may be several-fold higher than that achieved in the normal environment in which the protein is made. The function of the recombinant protein may subsequently be studied within the baculovirus-infected cell or after isolation of the product. The baculovirus expression system is widely used in industry and other research laboratories world-wide. In addition to the high levels of recombinant protein attained, the system is also popular because the material produced is usually biologically active. This is frequently a consequence of correct post-translational modification of the recombinant protein after it has been translated from the mRNA on insect cell ribosomes.

One of the limitations of the baculovirus expression system is that the process of inserting foreign genes into the virus genome is time consuming and labour intensive. Currently, two major methods are used. In the first, the baculovirus genome is maintained in *Escherichia coli* and foreign genes are inserted via a process of transposon mutagenesis after introducing another plasmid (the transfer vector) into the bacterial cell (Luckow et al., 1993). After recovering virus DNA from amplified bacterial cells, it is used to infect insect cells to produce a recombinant virus, which is free of any other virus genotype. In the second method, linear baculovirus DNA produced by digestion with a restriction endonuclease is mixed with the transfer vector and used to infect insect cells (Kitts and Possee, 1993). The transfer vector contains sequences from the virus genome that span the break in the DNA; these sequences flank the foreign gene to be inserted into the baculovirus genome. When the linear virus DNA and transfer vector enter the insect cells, recombination between the homologous sequences in both molecules effects transfer of the foreign gene into the baculovirus genome. Unfortunately, the recombinant virus recovered from the infected cells is usually contaminated with a low level (ca. 5%) of parental virus. This has to be removed by titrating the virus mixture (parental and recombinant) using a plaque assay in monolayers of insect cells to derive clonal stocks of the recombinant virus. A single operator, using either method, cannot easily make more than 25 recombinant viruses per week.

Neither of the methods described above is readily amenable to the high throughput generation of recombinant viruses; both require too many manipulations of plasmids, in viruses and cells (see Table 1). Such a method is now in demand because of the rapid deposition of sequence data from the human genome project (and other species, such as the mouse) in the databases world-wide. To interpret such vast stores of information, it will be necessary to express thousands of genes in alternative hosts (e.g. insect cells) to derive sufficient material to determine protein function.

TABLE 1

A comparison of methods for generating recombinant baculoviruses.

| Day | Bac-to-Bac | Linear DNA | New invention |
|---|---|---|---|
| 1. | Transform bacteria with transfer vector/amplify transformants on agar plates | Cotransfect insect cells with linear virus DNA/transfer vector | Cotransfect insect cells with bacterial virus DNA/transfer vector to produce P1 virus stock |
| 2. | | | |

TABLE 1-continued

A comparison of methods for generating recombinant baculoviruses.

| Day | Bac-to-Bac | Linear DNA | New invention |
|---|---|---|---|
| 3. | Pick bacterial colonies and amplify in liquid culture | Harvest medium from cotransfection and titrate in insect cells | |
| 4. | Purify recombinant Bacmid DNA and transfect insect cells for P1 stock | | Harvest P1 virus stock and infect more insect cells for P2 stocks |
| 5. | | | |
| 6. | | Stain plaque assays with X-gal and pick recombinant plaques. Infect insect cells for P1 stocks. | |
| 7. | Harvest P1 stock and infect more insect cells for P2 stock | | |
| 8. | | | |
| 9. | | Harvest P1 stocks and infect more insect cells for P2 stocks | Harvest P2 virus stock and titrate/infect insect cells to test recombinant protein production |
| 10. | | | |
| 11. | | | |
| 12. | Harvest P2 stock and titrate/infect insect cells to test recombinant protein production | | |
| 13. | | | |
| 14. | | Harvest P2 stock and titrate/infect insect cells to test recombinant protein production | |
| 15. | | | |
| 16. | | | |
| 17. | | | |
| 18. | | | |
| 19. | | | |

The inventors proposed that to develop an improved system for making recombinant baculoviruses would require the use of a defective form of the virus genome that could not, on its own, initiate replication after transfection into insect cells. However, when mixed with a plasmid transfer vector containing a foreign gene and a sequence capable of restoring replication gene, recombination between the two molecules would regenerate replication-competent virus.

This procedure was demonstrated in three experiments. In the first, lef-2 was deleted from the AcMNPV genome using a yeast system to manipulate the virus DNA. In the second, 6385 bp, containing ORF1629, protein kinase 1 and lef-1, was deleted from the AcMNPV genome which was maintained in bacterial cells. In the third, only a small part of ORF1629 was deleted from the virus genome maintained in bacteria. Defective AcMNPV genomes, maintained in yeast or bacterial cells, could be purified, mixed with a suitable rescue plasmid and used to transfect insect cells to recover infectious virus.

The inventors have inactivated the ORF1629 using bacterial cells as an intermediary host to maintain the AcMNPV genome.

This demonstrates that it is possible to generate and maintain replication deficient baculovirus in intermediary hosts. The virus can be rescued using a suitable rescue vector encoding a nucleic acid sequence to correct the deficiency. This has enabled a new method for cloning foreign genes in baculovirus to be identified.

The invention provides a method for cloning, and optionally expressing, a gene comprising the steps of:
(i) providing a replication deficient baculovirus vector;
(ii) providing a rescue vector encoding:
  (a) a nucleic acid sequence which is capable of restoring replication in the replication-deficient baculovirus vector; and
  (b) at least one gene to be cloned;
(iii) causing the replication-deficient baculovirus vector and rescue vector to recombine to produce a replication-enabled baculovirus vector comprising at least one gene to be cloned; and
(iv) growing the replication-enabled baculovirus vector within a suitable invertebrate cell.

Preferably the invertebrate cell is an insect cell, but other suitable invertebrate cells in which baculovirus may grow may be used.

By replication-deficient baculovirus vector we mean a DNA molecule based upon the genome of a baculovirus, but which has had at least one gene necessary for replication either deleted or mutated so that the baculovirus vector can no longer replicate on its own. For example, one or more functional genes such as lefs 1-12, dnapol, p143, p35, ie-1, ie-2, p47, ORF1629, and pp31 may have been deleted or mutated to inactivate them. These genes are known to be involved in baculovirus replication (Kool, et al, 1994; 1995; Lu et al. (1997); Lu and Miller 1995; Rapp, et al. 1998; Fan, et al. 1996; 1998; Todd, et al. 1995; 1996; McLachlin and Miller 1994; Guarino 1998).

The ability to replicate may be restored by recombination with a rescue vector comprising one of the functional genes, or a functional fragment or functional mutation thereof.

Preferably the baculovirus vector is based upon the genome of AcMNPV.

By gene we mean a nucleic acid sequence which is capable of being transcribed into a protein or peptide of interest. The gene to be cloned is preferably operably linked to regulatory elements necessary for expression of said gene within the invertebrate cell. Operatively linked refers to the juxta position such that the normal function of the components can be performed. Control sequences refers to DNA sequences necessary for the expression of an operatively linked gene in a particular host organism. Control sequences refers to DNA sequences which are suitable for eukaryotic cells, for example, are promoters, polyadenylation signals and enhancers. Preferably the control sequences include secretory signals to enable the product from the cloned gene to be secreted from the invertebrate cell.

Preferably the gene is under the control of a promoter selected from a baculovirus polyhedrin promoter and a baculovirus p10 promoter.

The advantage of the method of the invention is that it guarantees that substantially only recombinant virus containing the cloned gene is produced. This method avoids having to use time-consuming plaque assays or dot hybridisation to identify clones containing recombinant baculovirus. Accordingly, this allows the method to be automated using robotic devices and multi-well microtitre plates.

Preferably, the replication-deficient baculovirus vector comprises one or more replication elements to enable replication within one intermediate host. For example, if the intermediate host is a bacterial cell, then the vector may comprise a bacterial origin of replication, ori. If the intermediate host is a yeast, then the vector may comprise an autonoumous replication sequence, such as ARS1 and a centromere functional sequence, such a CEN1. Such replication elements are well known in the art. The intermediate host may be *Escherichia coli* or *Saccharomyces cerevisiae*.

The replication-deficient baculovirus vector may also comprise one or more selection genes to enable host cells comprising the replication-deficient baculovirus vector to be selected. Such selection gene may be antibiotic-resistance genes or nutritional. For example, antibiotic-resistance genes such as ampicillin, tetracycline, chloramphenicol, kanamycin or neomycin may be used in bacteria. The host cell will be selected according to the selection gene used in the vector. Therefore, a bacterial cell comprising a replication-deficient baculovirus vector containing a chloramphenicol resistance gene may be selected for by growing the cells in the presence of chloramphenicol. In yeast cells, nutritional genes such as URA3. Trp and His may be used. For example, if URA3 is used as a selection gene, then the host cell will be one that cannot grow in the absence of Uracil unless the baculovirus containing URA3 is present. Cells containing the vector can then be selected by growing the yeast cells in the absence of Uracil.

The rescue vector may similarly contain replication elements to enable it to be replicated within a desired host, together with selection markers to enable cells containing the rescue vector to be identified.

The rescue vector preferably contains one or more sites into which a gene to be cloned may be inserted. Methods for inserting foreign genes into vectors are well known in the art. For example, the vector may comprise a unique restriction endonuclease site into which the gene of interest may be inserted; preferably either side of the site are suitable promoter and termination sequences.

Rescue vectors which can insert multiple foreign gene coding sequences can be produced using techniques known in the art. For example, it is possible to construct a rescue vector comprising a polyhedrin gene promoter and transcription termination sequence upstream of, and in the opposite orientation to, a second polyhedrin gene promoter. It is also possible to insert a small DNA fragment encompassing the p10 promoter upstream, but in the opposite orientation of a polyhedrin promoter. The construction of multiple expression vectors is discussed in detail in the book by King and Possee (Supra).

The replication-deficient baculovirus vector and/or rescue vector may inserted into a suitable intermediate host by techniques known in the art. For bacterial cells, electroporation or calcium chloride mediated uptake of DNA may be used (Sambrook et al., 1989). For yeast cells methods such as treatment with lithium acetate may be used (Ito et al., 1983).

The replication-deficient baculovirus vector and rescue vector may be recombined either within the intermediate host or most preferably within the invertebrate cell.

Typically, the replication-deficient baculovirus vector and the rescue vector are purified and isolated from any host in which they reside since purification techniques are well known in the art. For example, a total DNA preparation may be undertaken followed by sucrose or caesium chloride density gradient purification. Each of the vectors are inserted into a suitable invertebrate cell by known techniques, for example as shown in King and Possee (1992). The two vectors then undergo recombination within the cell to produce a replication enabled baculovirus vector comprising at least one gene to be cloned. Such recombed baculoviruses are selected for since they are able to undergo replication and thus infect further cells and multiply.

Preferably the replication-deficient baculovirus lacks a gene coding for polyhedrin. This has the advantage that contaminating polyhedrin is not produced.

The invention also relates to a replication-deficient baculovirus vector for use in a method of the invention. Preferably such a vector comprises one or more nucleic acid sequences, which enable the vector to replicate within an intermediate host. Such sequences are described above.

A further aspect in the invention provides a rescue vector for use in a method according to the invention. Preferably the rescue vector is constructed as described above.

A still further aspect of the invention provided a kit for use in the method of the invention comprising a replication-deficient vector of the invention and/or a rescue vector according to the invention. The kit may additionally comprise one or more buffers, preservatives or stabilising agents to enable the vectors (s) to be stored or transported with minimal degradation of the vector. Such buffers, preservatives and stabilising agents are well known in the art.

Oligonucleotides used to construct recombinant viruses according to the invention are also provided.

The invention will now be described by way of example only, with reference to the following figures.

FIG. 1. Genomic organisation of parental and recombinant baculoviruses with modified polyhedrin and lef-2. (a) AcMNPV. Relative positions of lef-2, ORF603 and polyhedrin. (b) AcAUC. The insertion of the ARS-URA3-CEN4 cassette (not drawn to scale) relative to a deletion in polyhedrin. (c) AcΔ lef-2.sup4-o. The sup4-o was inserted into lef-2 via homologous recombination in yeast cells harbouring AcAUC. Selected restriction enzyme sites are shown with appropriate genomic co-ordinates (Ayres et al., 1994).

Figure 2:
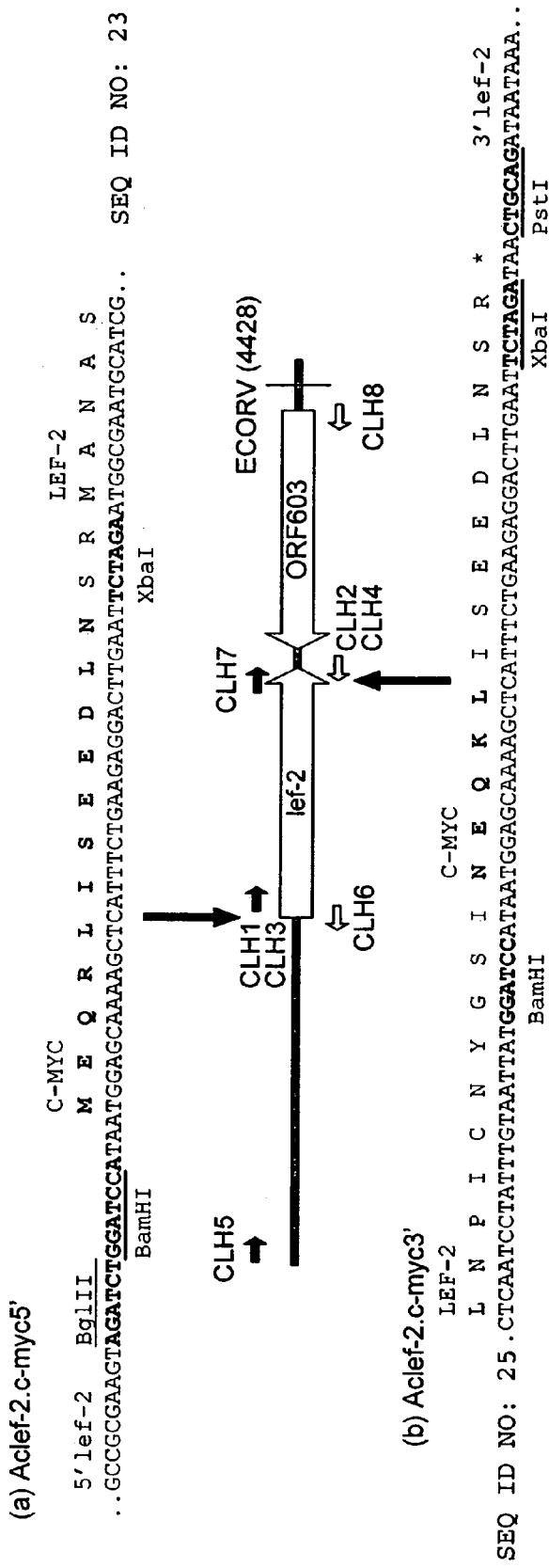

FIG. 2. Genomic organisation of viruses with C-MYC added to LEF-2. (a) Aclef-2.c-myc5' The c-myc coding region was inserted at the 5' end of lef-2. The C-MYC sequence is shown as bold text above the coding region. The additional amino acids introduced between C-MYC and LEF-2 via the XbaI site are italicised. (b) Aclef-2.c-myc3'. The c-myc coding region was inserted at the 3' end of lef-2. The positions of oligonucleotide primers used to generate selected DNA fragments in the lef-2 region for construction of the modified gene are indicated above and below the central genomic map.

Figure 3:
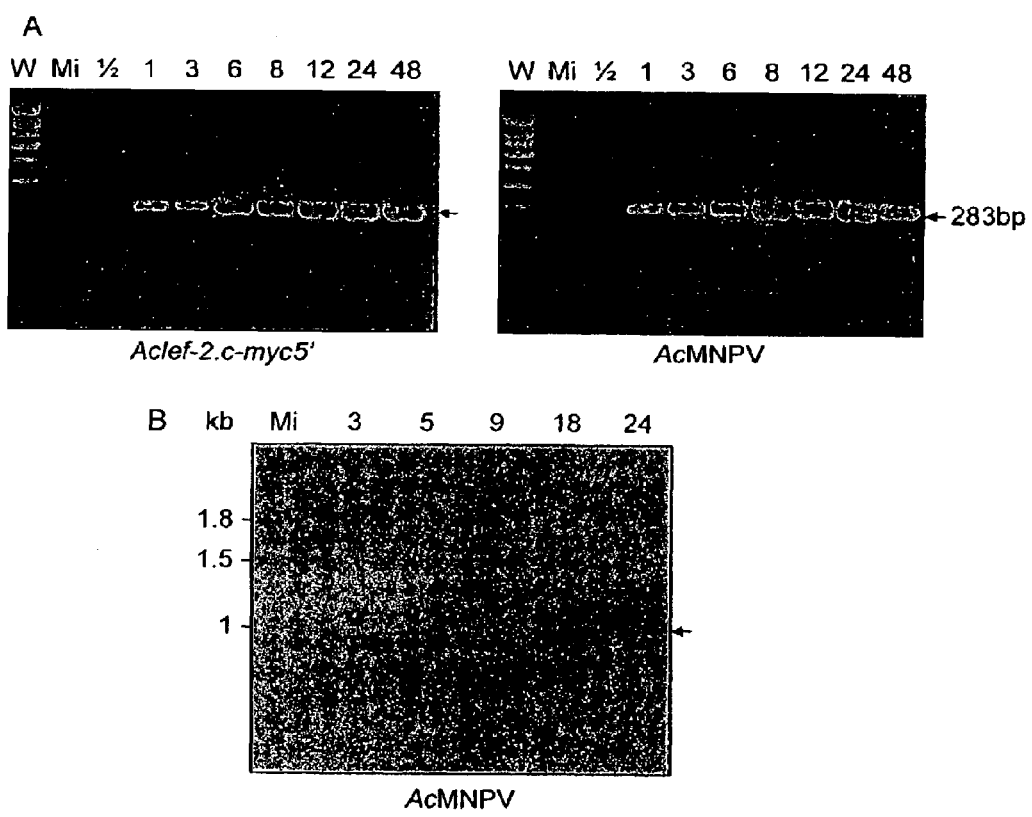

FIG. 3. Temporal Expression of lef-2 Transcript.

(A) mRNA were extracted from Sf-21 cells either mock-infected (Mi), infected with Acc-myclef-2 or AcMNPV C6 at a m.o.i. of 20, at the times (hours post infection) indicated above the lanes. mRNA (100 ng) were subjected to RT-PCR using two internal specific primers of lef-2. The size of the specific RT-PCR product is indicated on the right. The W lane corresponds to the "smartladder SF" size marker from Eurogentec (1000, 800, 700, 600, 500, 400, 300, 200 and 100 bp from the top to the bottom).

(B) mRNAs were extracted from Sf-21 cells either mock infected (Mi) or infected with AcMNPV-C6 or Acc-myclef-2 at a m.o.i. of 20, at times (hours post infection) indicated above the lanes and subjected (2 µg per lane) to Northern blot. The sizes of the markers are shown on the left of the blot and the location of the major band hybridising with the lef-2 probe is indicated by an arrow on the right.

Figure 4:
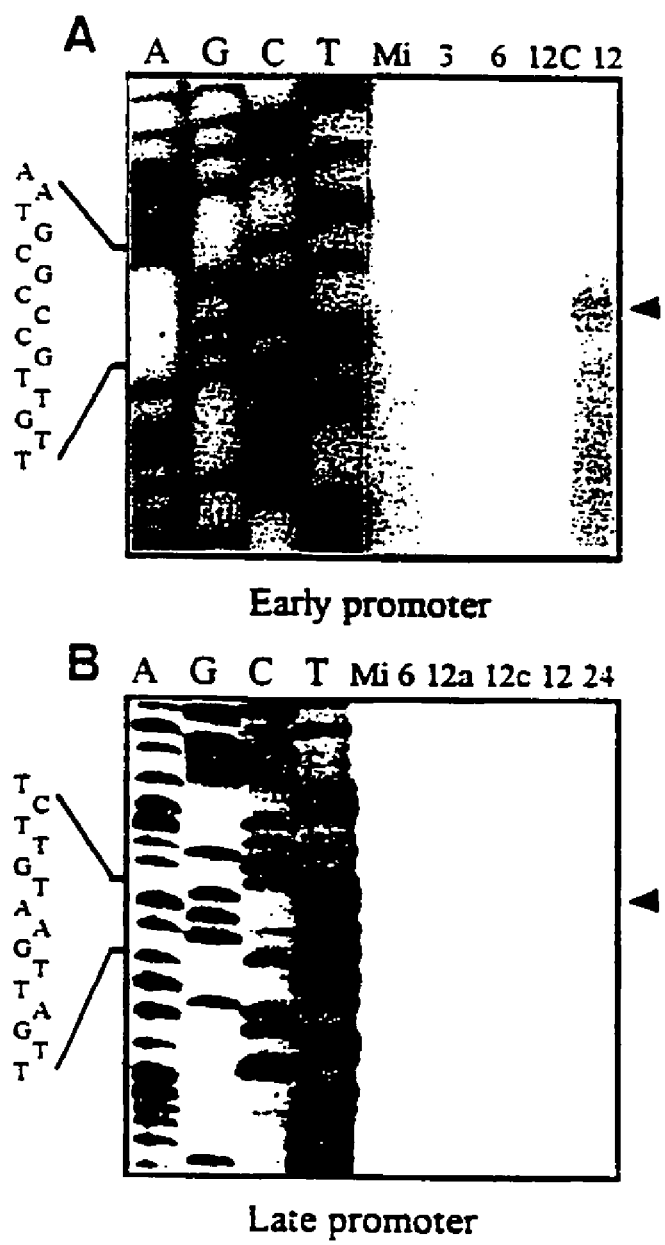

FIG. 4. 5' mapping of the lef-2 transcripts. Total RNA from mock infected or Acc-myclef-2-infected cells were extracted at different times post infection and incubated with primer lef-2 PE4 (A) or lef-2 PE3 (B) depending on the promoter mapped (early or late). The reaction products were separated on a 6% sequencing gel, in parallel with a sequencing ladder generated with the same primer. Products are indicated on the right by arrows. Sequence and initiation sites are shown on the left. 12a: treatment with aphidicolin. 12c: treatment with cycloheximide.

Figure 5:
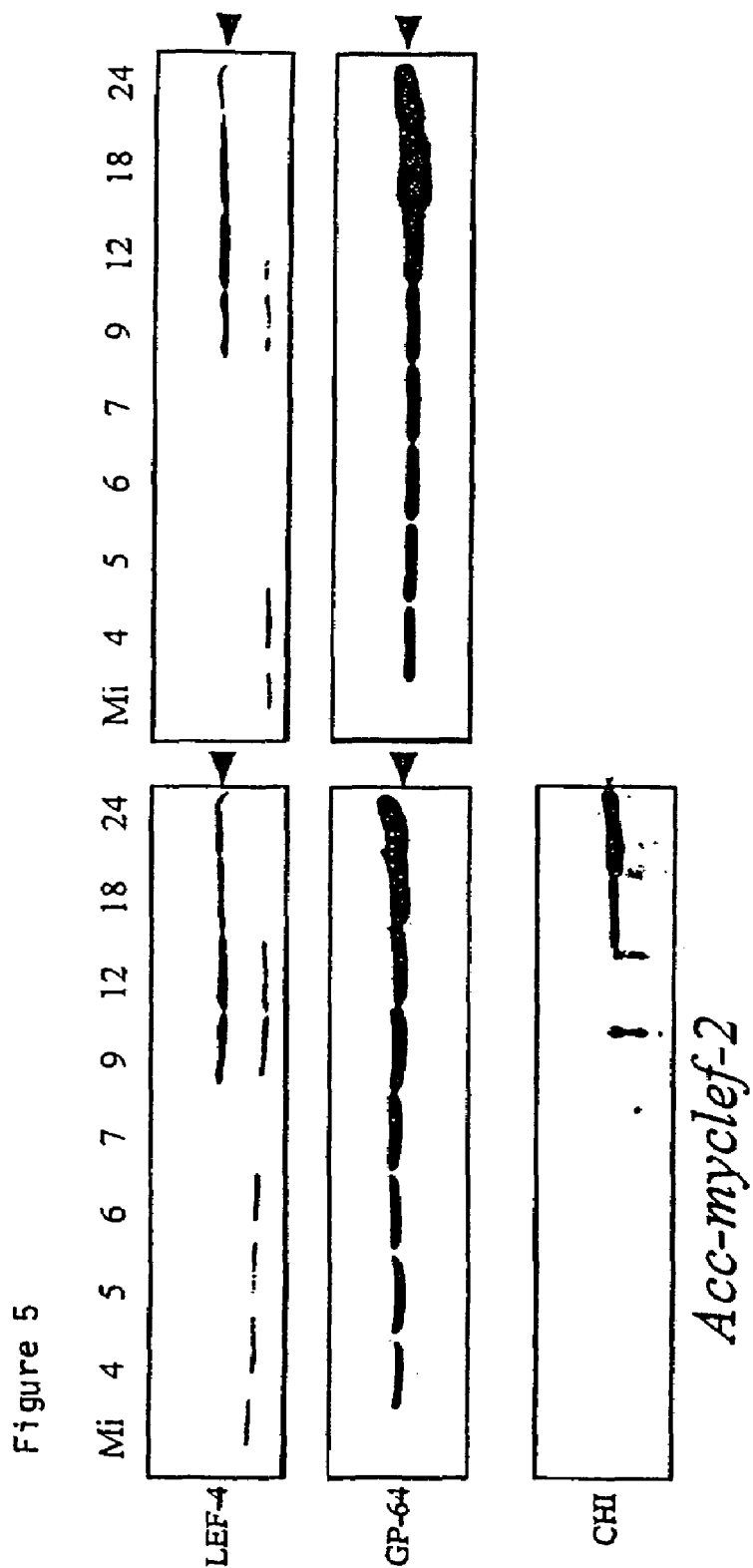

FIG. 5. Expression of LEF-4, GP-64 in Acc-myclef-2 and AcMNPV C6-infected Sf-21 cells and expression of CHI in Acc-myclef-2-infected cells.

Western blot analysis of steady-state levels of selected early (LEF-4) and late (GP-64 and chitinase) proteins in Acc-myclef-2 and wt-infected Sf-21 cells from 4 to 24 hr p.i. The protein bands are indicated by arrows. The numbers above each lane indicate time post infection and the proteins analysed is indicated on the left.

Figure 6:
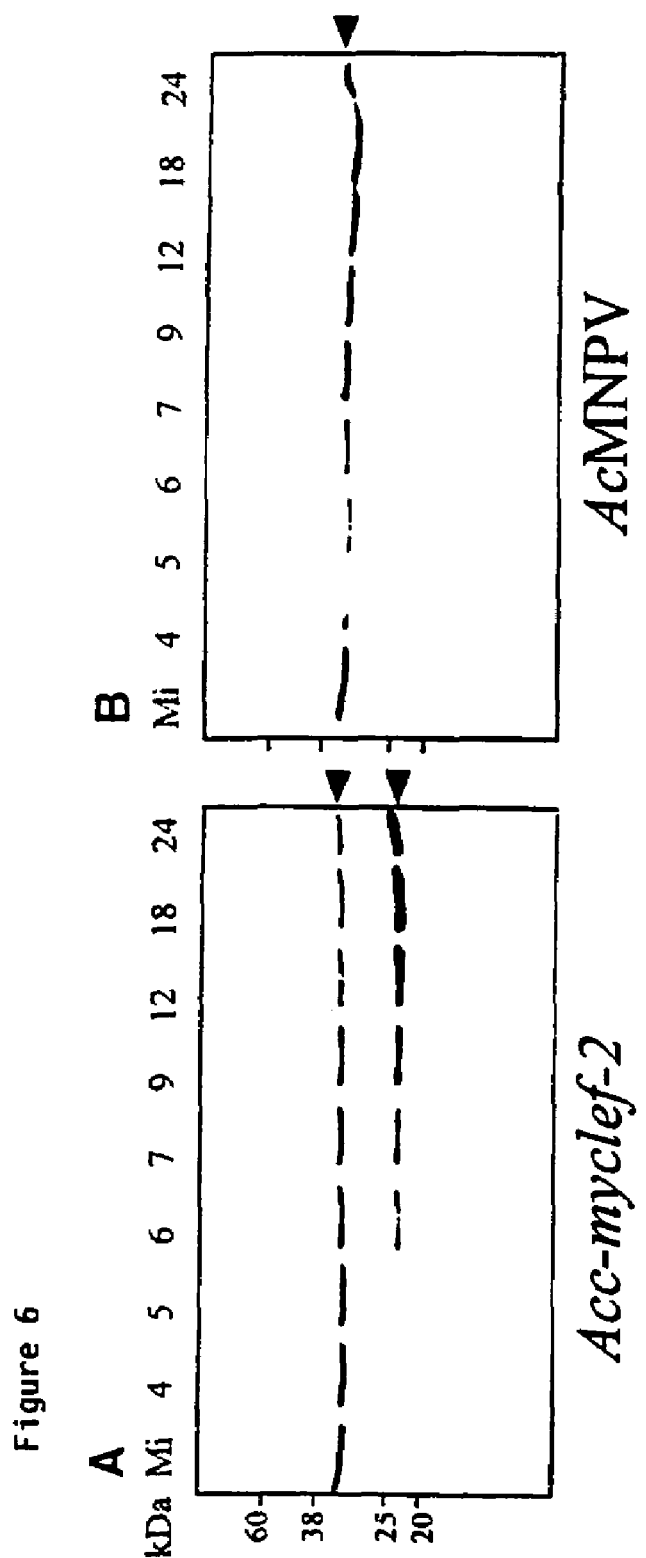

FIG. 6. Western Blot Analysis of Tagged-lef-2 Product in Acc-myclef-2 or AcMNPV C6-infected Sf-21 Cells.

Western blot analysis of the tagged-lef-2 product in Acc-myclef-2 or AcMNPV-C6-infected Sf-21 cells from 4 to 24 hr p.i. C-MYCLEF-2 protein was identified using the monoclonal anti-C-MYC antibody (clone9E10) and detected with a chemoluminescent substrate. The corresponding times post infection (hr p.i.) are indicated above the lanes (Mi, mock infected). Size standards are indicated on the left and immunoreactive proteins are shown by arrows.

Figure 7:
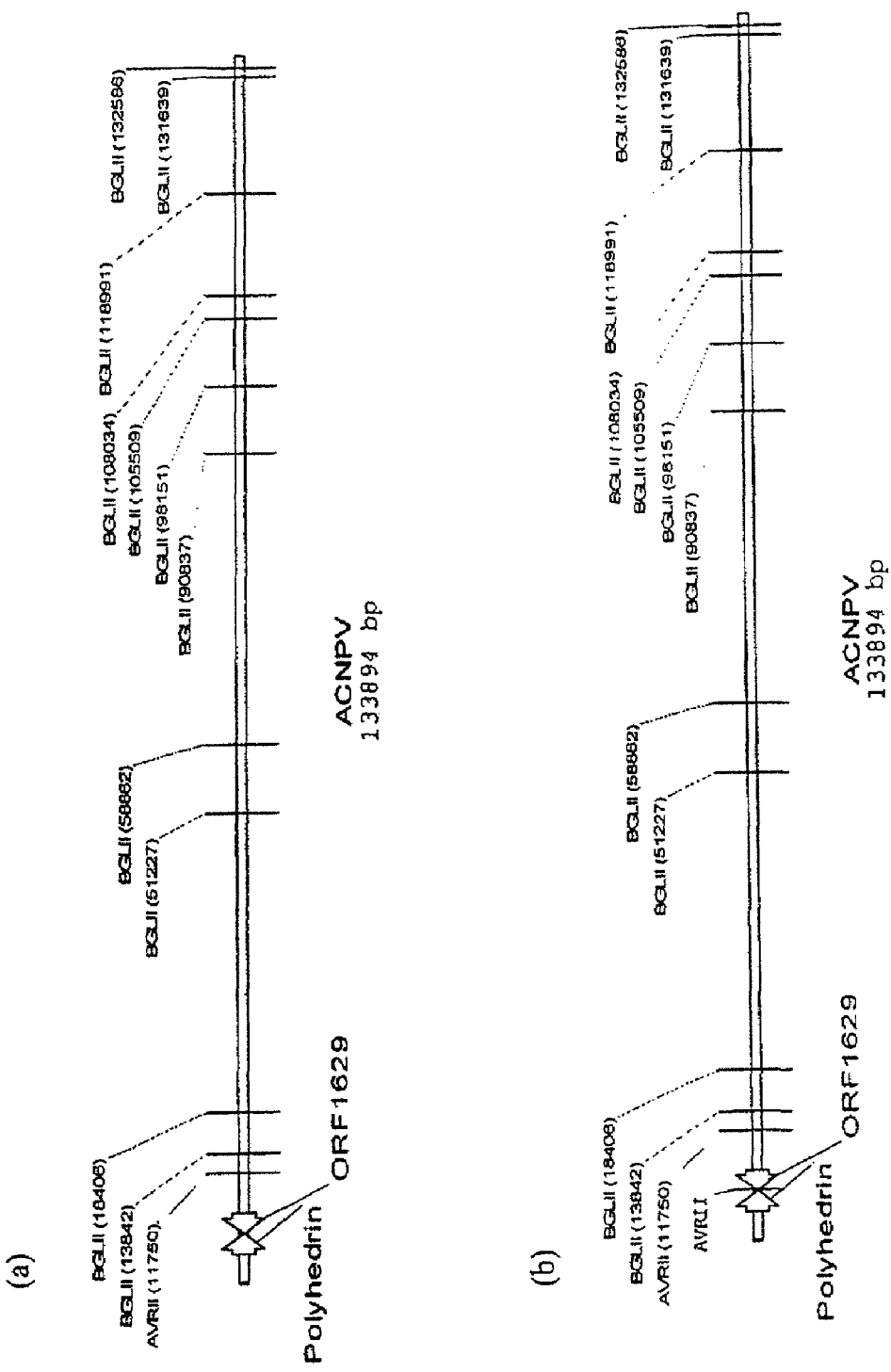

FIG. 7. Genomic organization of parental and recombinant baculoviruses with modified ORF1629. (a) Genetic organization of AcMNPV showing positions of BglII and AvrII restriction enzyme sites. The positions and orientation of the polyhedrin and ORF1629 genes are indicated; not drawn to scale. (b) Genomic organization of A1AvrII showing position of second AvrII site added to the virus genome. The polyhedron gene in this virus is non-functional as it lacks the first 150 nucleotides of the coding region and cannot make a mature protein.

MATERIALS AND METHODS

Insect Cells and Viruses

*Spodoptera frugiperda* IPLB-Sf21 cells were propagated at 28° C. in TC100 medium supplemented with 10% (v/v) foetal calf serum (FCS). AcMNPV C6 and other recombinant viruses were amplified and titrated according to standard protocols (King and Possee, 1992). AcMNPV DNA replication was blocked by treating the virus-infected cells with aphidicolin (5 µg/ml; Sigma, USA) while protein synthesis was inhibited by using cycloheximine (200 µg/ml; Sigma, USA) according to a recent modification (Ross and Guarino, 1997).

Yeast Based System

Yeast Cells and Transformation

The *Saccharomyces cerevisiae* strain used in this study was y657 (mat α his3-11, 15 trp1-1 ade2-1 leu2-3, 112 ura3-52 can1-100 his4:HIS3; Newman and Norman, 1991) kindly provided by G. Patel, ICRF, London, UK. This was grown in rich medium (yeast extract, peptone, dextrose [YPD]) at 30° C. Yeast strains maintaining the baculovirus genome were grown in minimal medium supplemented with adenine (20 µg/ml), histidine (20 µg/ml), leucine (60 µg/ml), tryptophan (20 µg/ml) and casamino acids (10 mg/ml) (Sherman, 1991). Canavanine resistant colonies were selected on minimal medium plates containing 60 µg/ml canavanine sulphate (Sigma, UK).

Transformation of yeast with the AcMNPV genome and other plasmids was carried out with the lithium acetate method (Ito et al., 1983) using high molecular weight DNA as a carrier (Schiestl and Gietz, 1989). Briefly, y657 cells were grown in 5 ml YPD medium to saturation. This culture was used to inoculate 250 ml YPD medium, supplemented with 30 µg/ml adenine hemisulphate and the cells grown overnight at 30° C. to a cell density corresponding to $OD_{600}$=0.3 to 0.5. The cells were harvested by centrifugation (4000 g; 5 min) and washed with 10 ml sterile water. The cells were then resuspended in 1.5 ml freshly prepared lithium solution (10 mM Tris-HCl, pH7.5/1 mM EDTA/0.1M lithium acetate, pH7.5). To transform the yeast cells, 200 µg carrier DNA (salmon sperm DNA boiled 3', then snap-chilled) was mixed with 5 µg transforming DNA in a volume of less than 20 µl. The yeast suspension (200 µl) was added to the DNA along with 1.2 ml freshly prepared PEG solution (40% PEG 3350/10 mM Tris-HCl, pH7.5/1 mM EDTA/0.1M lithium acetate, pH7.5). The mixture was shaken at 30° C. for 30 minutes, then heat-shocked at 42° C. for exactly 15 minutes. The cells were pelleted and resuspended in 1 ml TE buffer (10 mM Tris-HCl, pH7.5/1 mM EDTA). Aliquots (200 µl) were spread onto minimal media plates and incubated at 30° C. for 3-4 days.

Plasmid and Recombinant Virus Constructions

The plasmid pAcAUC, containing the ARS (A), URA3 (U) and CEN (C) sequences at the polh locus (Patel et al., 1992) was mixed with Bsu36I-linearised BacPAK5 DNA (Kitts and Possee, 1993), in the presence of lipofection and used to transfect Sf21 cells (King and Possee, 1992). Progeny virus was plaque purified and amplified to produce polyhedrin-negative stocks (AcAUC) containing the yeast AUC elements. Infectious virus DNA was purified and used to transform y657 cells to yield yAcAUC.

The vector pUC8/6/8 (Possee, 1986), containing the AcMNPV EcoRI-I region was used to generate a plasmid containing a modified lef-2 and the sup4-o yeast selectable marker. An octanucleotide BglII linker was inserted at the EcoRV site upstream of polh to create pUC8/6/8-BglII. This plasmid was digested with HindIII, recircularised and amplified in bacteria, then digested with SalI (FIG. 1). The ends of the linear DNA were repaired with the Klenow fragment of DNA polymerase and ligated with a blunt-ended DNA fragment containing sup4-o to produce plef2Δ.sup4-o. (The sup4-o was originally obtained from G. Patel and inserted into the EcoRI site of pUC118 to provide a convenient supply). Lithium acetate-treated yAcAUC yeast cells were transformed with plef2Δ.sup4-o and grown on minimal medium plates lacking uracil and adenine. Small white colonies were replica plated on the same medium in the presence or absence of canavanine sulphate. Canavanine sensitivity indicated that sup4-o was inserted into the virus genome maintained within the yeast cell.

Yeast DNA Extraction and Transfection of Insect Cells

Total yeast DNA was prepared as described (Patel et al., 1992) and layered onto a 5-20% continuous sucrose gradient in STE (200 mM NaCl/10 mM Tris pH7.5/1 mM EDTA). The gradient was centrifuged at 35,000 rpm for 3 hours at 20° C. in a Beckman SW41 rotor. The gradient was then harvested in 0.5 ml fractions by downward displacement. The DNA in each fraction was ethanol precipitated, pelleted and resuspended in 50 μl TE pH 7.5. Aliquots (10 μl) of each DNA fraction were placed in sterile polystyrene bijou bottles with 0.5 ml TC100 lacking FCS; on occasion, 500 ng of a rescuing plasmid (pUC8/6/8) was included. An additional 0.5 ml TC100 minus FCS containing 5 μl lipofectin was added to each DNA solution and the mixtures were incubated at room temperature for 15 to 30 minutes. Thereafter, $3 \times 10^5$ Sf21 cells

TABLE 2

| Oilgo | Sequence[a] | Strand[b] | REN site[c] | Position | SEQ ID NO. |
|---|---|---|---|---|---|
| c-myc1 | GATCCATAATGGAGCAAAAGCTCATTTCTGAAGAGGACTTGAAT<u>TCTAGA</u>TAACTGCA | + | XbaI | N/A | 1 |
| c-myc2 | GTTA<u>TCTAGA</u>ATTCAAGTCCTCTTCAGAATGAGCTTTTGCTCCATTATG | − | XbaI | N/A | 2 |
| CLH1 | *CGGC<u>AGATCT</u>ATAATGGCGAATGCA* | + | BglII | 3089-3100 | 3 |
| CLH2 | *GCCA<u>GGATCC</u>ATAATTACAAATAGGATTGAG* | − | BamHI | 3698-3718 | 4 |
| CLH3 | *CGGC<u>TCTAGA</u>ATGGCGAATGCATC* | + | XbaI | 3089-3102 | 5 |
| CLH4 | *GCCG<u>CTGCAG</u>TCAATAATTACAAATAGG* | − | PstI | 3704-3721 | 6 |
| CLH5 | *GGCC<u>GGTACC</u>GAGTTCGTTGACGC* | + | KpnI | 2334-2347 | 7 |
| CLH6 | *CGCG<u>AGATCT</u>ACTTCGCGGCTTCTCGCACC* | − | BglII | 3069-3088 | 8 |
| CLH7 | *GGCC<u>CTGCAG</u>ATAATAAACAATTATAAAT* | + | PstI | 3722-3741 | 9 |
| CLH8 | *CGCG<u>AAGCTT</u>AGCAACTATATATT* | − | HindIII | 4411-4424 | 10 |
| Lef-2PE3 | AGCTCGTGCCGGAACGCGTGCACAGATCG | − | | 2886-2915 | 11 |
| Lef-2PE4 | TGTAGTCGGCAGTTCATTTGGGCGTGATCG | − | | 2966-2995 | 12 |
| Lef-2RT1 | AGAAAACAATGTACCGCGCGGCGG | + | | 3438-3462 | 13 |
| Lef-2stop | ATGC<u>GAATTC</u>TCAATAATTACAAATAGGATTG | − | EcoRI | 3700-3721 | 14 |

[a]The first nucleotide corresponding to AcMNPV sequence is shown.
[b]Relative to the coding strand of lef-2.
[c]The restriction enzyme site is underlined in the sequence of the oligonucleotide.

To construct transfer vectors containing a c-myc epitope tag at either end of lef-2, oligonucleotides c-myc1 and c-myc2 were constructed (Table 2). These specified the sense and anti-sense c-myc sequences respectively. The oligonucleotides were annealed to create the double stranded c-myc coding region with BamHI and PstI cohesive ends. The epitope coding region also included an XbaI site-directly upstream of the stop codon. The annealed oligonucleotides were inserted into a modified pUC118 plasmid (containing a BglII site directly upstream of the BamHI site) between the BamHI and PstI sites to derive pUC.c-myc. Copies of the lef-2 coding region were created using PCR. These possessed either 5'-BamHI and 3'-BglII ends and no TGA stop codon, or 5'-XbaI and 3'-PstI ends including the TGA stop codon. These were inserted into pUC.c-myc separately at the BamHI or the XbaI and PstI sites respectively to derive two plasmids in which the c-myc epitope was either upstream or downstream of lef-2. PCR was then used to derive upstream and downstream regions of lef-2 possessing 5'-KpnI, 3'-BglII or 5'-PstI, 3'-HindIII ends respectively. These were inserted at either end of the c-myc-tagged lef-2 in both plasmids to derive pAclef-2.c-myc5' and pAclef-2.c-myc3' (FIG. 2).

in 35 mm cell culture dishes were transfected as described by King and Possee (1992). The dishes were incubated at 28° C. for 6 days and monitored daily for signs of viral infection. The virus-containing medium was then harvested and titrated in a plaque assay.

Western Blot and Immunoflu Rescence Analysis

Monolayers of $10^7$ Sf21 cells were infected with AcMNPVC6 or Aclef-2.c-myc5' at a multiplicity of infection (m.o.i.) of 20 or mock-infected with medium. Cells were harvested at various times, pelleted, washed twice with PBS and lysed in dissociation mixture (Laemmli, 1970). Protein samples (equivalent of $3 \times 10^6$ cells) were then loaded and separated by SDS-PAGE and transferred onto nitrocellulose membranes. The membranes were incubated overnight in Tris-NaCl buffer (TBS: 137 mM NaCl; 20 mM Tris-HCl, pH 7.6) containing 10% dried milk and 0.1% Tween-20. C-MYC monoclonal (clone 9E10), GP64-EFP monoclonal (AcV5), LEF-4 polyclonal and CHI [AcMNPV chitinase] polyclonal antisera have been described previously (Evan et al., 1985; Blissard and Rohrmann, 1989; Durantel et al., 1998a; b; Hawtin et al., 1995, respectively).

Western blots were performed with appropriate dilutions of polyclonal or monoclonal antibodies. Immunoreactive proteins were detected using the appropriate secondary antibody linked to the peroxidase (Sigma, USA) followed by incubation with a chemoluminescent substrate (Amersham, UK), according to the manufacturer's instructions.

Immunofluorescence staining was performed as described previously (Durantel et al., 1998b) with an important modification. First and secondary antibodies were applied twice in order to amplify the staining. The preparations were examined under a Zeiss LSM410 confocal laser scanning microscope.

RNA Procedures

Messenger RNA isolation, Northern blot, primer extension, RT-PCR and 3'RACE (rapid amplification of cDNA ends) were described previously (Durantel et al., 1998a; b). Extraction of total RNA was performed using the RNeasy midi kit following the manufacturer's instructions (Qiagen, USA). The synthetic oligonucleotides used in primer extension were lef-2PE3 and lef-2PE4; in RT-PCR, lef-2RT-1 and lef-2stop; in RT-PCR, lef-2RT1 and oligo(dt). The sequence of each primer is listed in Table 1, with further information on its position relative to the AcMNPV genome.

Bacterial Based System

Bacterial Cells and Plasmid Purification

*Escherichia coli* DH5αF' were made competent for transformation with plasmid DNA by treating logarithmic phase cells with calcium chloride (King and Possee, 1992). The *E. coli* DH10B cells were made-competent for electroporation as described by Sambrook et al. (1989). Plasmids were purified from bacterial cultures using Qiagen gravity flow columns (Qiagen Ltd., Crawley, UK) or caesium chloride gradients (King and Possee, 1992). Baculovirus DNA was isolated from bacterial cells using a modified method and buffers recommended for the purification of plasmid DNA from *E. coli* by Qiagen. Briefly, bacterial cells grown to stationary phase after overnight incubation at 37° C. were pelleted, resuspended in 300 µl P1 buffer and treated with ribnuclease A (100 µg/ml) before lysis with an equal volume of P2 buffer. After 5 min incubation at room temperature, 300 µl P3 buffer was added to the lysate and left on ice for 15 min. Thereafter, cellular debris was pelleted and the supernatent fraction, containing baculovirus DNA, precipitated with 0.7 vol propanol. The DNA was pelleted, washed twice with 75% ethanol, briefly dried and resuspended in 40 µl TE buffer (10 mM Tris-HCl, pH 7.8; 0.1 mM EDTA).

Plasmid Construction and Recombinant Virus Preparation

Acp10Bac. The plasmid transfer vector pAcUW1 (Weyer et al, 1990) was digested with HindIII and then treated with calf intestinal phosphatase (CIP) according to Sambrook et al. (1989). The plasmid pBace3.6 was digested with HindIII to remove the bacterial origin of replication and chloramphenicol resistance gene. The fragment containing these elements (6380 bp) was isolated by fractionating the digested plasmid using an agarose gel, excising the appropriate DNA band and removing the agarose with a Qiagen spin column. The concentration of the DNA fragment was assessed by analysis on an agarose gel. It was then ligated with the HindIII-digested, CIP-treated pAcUW1 and used to transform *E. coli* DH5αF' to derive pAcUW1.Bac, which was amplified and purified according to standard protocols. The plasmid (0.5 µg) was then mixed with Bsu36I-digested AcUW1.lacZ virus genomic DNA (0.1 µg) and used to transfect Sf21 cells in the presence of lipofectin (King and Possee, 1992). The virus progeny was titrated in a plaque assay using Sf21 cells. The plaques were stained with X-gal at 4 days p.i. and those failing to exhibit a blue colour the next day were isolated and the virus amplified in Sf21 cells. This was designated Acp10Bac. Virus DNA was prepared from purified virus particles according to standard procedures (King and Possee, 1992) and used to transform *E. coli* DH10B cells via electroporation.

BacPAK6p10Bac. Virus DNA isolated from Acp10Bac was mixed with pBacPAK6 (Kitts and Possee, 1993) and used to cotransfect Sf21 cells. The virus progeny was titrated in a plaque assay using Sf21 cells and at 4 days p.i., plaques staining blue in the presence of X-gal and lacking polyhedra were isolated (BacPAK6p10Bac). The recombinant viruses were amplified in Sf21 cell and virus DNA purified as before.

AL1AvrII. The plasmid transfer vector pAcAL1 was digested with SwaI and SnaBI, then subsequently treated with CIP. This modified plasmid was then ligated with two pairs of synthetic oligonucleotides (Swa1F and R; AvrII F and R—see Table 3), phosphorylated at their 5' ends. The ligation mixes were used to transform *E. coli* DH5αF', which were subsequently plated onto agar plates containing ampicillin. Bacterial colonies were amplified in liquid medium and plasmid DNA purified. This was digested with SwaI and SnaBI to confirm that the synthetic oligonucleotides had been inserted in the correct orientation. Plasmids with the oligonucleotides in the correct orientation were designated pAcAL1SwaIF/R.AvrIIF/R. The modified regions of these plasmids were subsequently sequenced to confirm that the oligonucleotides had been synthesised correctly. pAcAL1SwaIF/R.AvrIIF/R was then digested with SnaBI and AvrII, treated with CIP and ligated with another pair of synthetic oligonucleotides (SnaBIF and R—see Table 3). The ligation mixture was used to transform *E. coli* DH5αF' as described above. The ampicillin-resistant colonies were amplified, plasmid DNA prepared and sequenced across the modified region to confirm the insertion of the predicted oligonucleotides. Plasmids with the correct sequences were designated pAcAL1AvrII, to denote addition of the synthetic AvrII site within the 3' end of the ORF1629. One such plasmid was mixed with Bsu36I-digested BacPAK6p10Bac and used to cotransfect Sf21 cells to derive AL1AvrII after plaque purification of the virus progeny. This virus was amplified further in Sf21 cells and genomic DNA purified as before.

AcORF1629⁻. BacPAK6p10Bac genomic DNA was digested with Bsu36I and then treated with the large sub-unit of the *E. coli* DNA polymerase 1 (Klenow) in the presence of dATP, dGTP, dCTP and TTP (Sambrook et al., 1989) to repair the ends of the DNA molecules. The reaction mixture was heated to 60° C. for 20 min, prior to subsequent storage at 4° C. A sample of the virus DNA was then ligated to recircularise the genome, before electroporation of DH10B cells and selection on agar plates. Chloramphenicol-resistant colonies were amplified in liquid cultures and virus DNA purified.

TABLE 3

Synthetic oligonucleotides used to construct recombinant viruses

| Oligo | Sequence (5'-3') | SEQ ID NO. |
|---|---|---|
| SwaIF | AAATTCAGATATAAAGACGCTGAAAATCATTTG | 15 |
| SwaIR | TGATTTTCAGCGTCTTTATATCTGAATT | 16 |
| AvrIIF | ATTTTCGCTCTAACATACCACCCTAGGGATGTAC | 17 |
| AvrIIR | GTACATCCCTAGGGTGGTATGTTAGAGCGAAAATCAAA | 18 |

TABLE 3-continued

Synthetic oligonucleotides used to construct recombinant viruses

| Oligo | Sequence (5'-3') | SEQ ID NO. |
|---|---|---|
| SnaBIF | CTAGGGATTATAAATTTAATGAATTATTAAA ATAC | 19 |
| SnaBIR | GTATTTTAATAATTCATTAAATTTATAATCC | 20 |

Results

P Production of a Recombinant Baculovirus DNA Containing a Deletion Within the lef-2 Gene Using Yeast Cells as Intermediate Host.

A recombinant virus (AcAUC), containing the ARS, CEN and URA3 sequences at the polh locus, was produced to enable propagation of viral DNA in yeast cells. The genetic organisation of this virus is shown in FIG. 1. The correct insertion of the three yeast elements in the AcMNPV genome was confirmed by Southern hybridisation analysis (data not shown).

Virus DNA was extracted from purified AcAUC budded virus particles and used to transform the yeast strain y657. Yeast cells containing the AcAUC DNA were selected on dropout plates lacking uracil. Yeast cells were transformed at an efficiency of approximately $2\times10^5$ colonies per μg transforming DNA. Total DNA was extracted from amplified yeast cultures (yAcAUC), fractionated on sucrose gradients and used to transfect *S. frugiperda* cells. After six days, it was determined that the transfected cell culture medium contained $5\times10^4$ pfu/ml. Cell cultures transfected with 100 ng AcMNPV DNA produced $9.7\times10^5$ pfu/ml over the same period. Subsequent amplification of AcAUC derived from yeast in insect cells produced virus stocks of normal titre ($>10^7$ pfu/ml).

In order to delete lef-2 from AcAUC DNA maintained in yAcAUC, we produced a transfer vector (plef-2.sup4-o) containing sup4-o in lieu of lef-2 (FIG. 1c). Yeast stains with ochre mutations in both ade2 and can1 grow as pink colonies in the absence of adenine and are insensitive to canavanine. Suppression of these mutations by sup4-o causes the production of white colonies that are sensitive to canavanine. The yAcAUC cells were transformed with plef-2.sup4-o and colonies containing sup4-o were selected by growth on dropout plates lacking uracil and adenine. Adenine independent colonies (white) were then replica-plated onto dropout plates lacking uracil but containing canavanine sulphate. Colonies sensitive to canavanine were retro-selected. Twelve yeast colonies were isolated with the correct phenotype of ura3+ and sup4-o+ by replica plating and amplified in liquid culture.

Transfection of Insect Cells with Viral DNA Isolated from ura3+, sup4-o+ Yeast Colonies.

Virus DNA was isolated from twelve yeast clones identified as ura3+ and sup4-o+. Each sample was used to transfect *S. frugiperda* cells in the presence or absence of pUC8/6/8, a plasmid containing an intact lef-2 (Possee et al., 1991). The addition of this plasmid to the transfection mix was predicted to rescue the expected deletion in lef-2, via homologous recombination in insect cells, and permit virus replication. Nine out of the twelve DNA preparations caused infection of the *S. frugiperda* cells irrespective of the presence of the rescuing plasmid (data not shown). When each of the other three DNA preparations

TABLE 4

Transfection of Sf21 cells with virus DNA

| Viral DNA | pUC8/6/8 | Titre after transfection (p.f.u./ml)[a] | Titre after progeny virus amplification (p.f.u/ml)[b] |
|---|---|---|---|
| AcMNPV(100 ng) | − | $2\times10^6$ | $5\times10^7$ |
| yAcΔlef-2.sup4-o[9] | − | ND | ND |
| yAcΔlef-2.sup4-o[9] | + | $9\times10^3$ | $5\times10^7$ |
| yAcΔlef-2.sup4-o[10] | − | ND | ND |
| yAcΔlef-2.sup4-o[10] | + | $5\times10^4$ | $5\times10^7$ |
| yAcΔlef-2.sup4-o[21] | − | ND | ND |
| yAcΔlef-2.sup4-o[21] | − | $6\times10^4$ | $5\times10^7$ |

[a]Progeny virus was titrated 6 days after transfection of Sf21 cells.
[b]Infectivity of virus stocks after amplification in Sf21 cells.

(AcΔ.lef-2.sup4-o[9], [12] or [21]) were used to transfect Sf21 cells without pUC8/6/8, productive infection of the cells was not observed. However, co-transfection of insect cells with each of these DNA preparations and the rescuing plasmid resulted in low levels of infectious budded virus production (Table 4). In comparison with insect cells transfected with 100 ng AcMNPV DNA, 33-200-fold less virus was produced. When these primary virus stocks were amplified in suspension cultures of insect cells, however, normal virus tires were attained for all samples (Table 4).

Production of a c-myc-tagged AcMNPV lef-2

The AcΔ.lef-2.sup4-o[9] was used to derive a recombinant virus with a human C-MYC coding region added to that of lef-2, to permit the identification of LEF-2 in virus-infected cells. The C-MYC epitope or tag comprises 12 amino acids (SEQ ID NO: 26 NH$_2$-MEQKLIEEDLNSRo-COOH), which can be recognised by a monoclonal antibody (9E10; Evan et al., 1986). It was not known whether addition of this epitope would affect the folding and/or the activity of LEF-2 when added to either end of the protein. Two transfer vectors were constructed containing the c-myc coding sequence at either the 5' (pAclef-2.c-myc5') or 3' (pAclef-2.c-myc3') ends of the lef-2 coding region (FIG. 2). These were used individually to co-transect insect cells with AcΔ.lef-2.sup4-o[9] DNA isolated from yeast cells. After 6 days, the cell culture medium for each sample was titrated in a plaque assay to monitor virus production. Infectious virus (Aclef-2.5'c-myc) was only produced by cells co-transfected with AcΔ.lef-2.sup4-o[9] and pAclef-2.c-myc5'. This was amplified further in insect cells to derive a virus stock (Aclef-2. c-myc5') of comparable titer to that produced by AcMNPV (ca. 1–$2\times10^8$ p.f.u./ml)

To confirm that the c-myc coding region was present at the 5' end of lef-2 in Aclef-2.c-myc5', total DNA was extracted from virus-infected cells and the lef-2 region amplified by PCR. The resulting DNA fragment was digested with BamHI to detect the extra site inserted at the start of lef-2 when c-myc was present. All three viruses exhibited the presence of c-myc at the 5'-end of lef-2 (data not shown).

Analysis of lef-2 Transcription

The production of Aclef-2.c-myc5' virus stocks of normal infectivity suggested that transcription of lef-2 was not affected by the addition of the c-myc sequences. This was confirmed by analysing the temporal regulation of lef-2 using RT-PCR to amplify purified mRNA extracted from AcMNPV-, Aclef-2.c-myc5'- or mock-infected cells. Two oligonucleotide primers (lef-2RT1 and lef-2stop) internal to lef-2 were used to amplify a 283-bp fragment. For both virus infections, lef-2-specific mRNA sequences were amplified as early as 1 hr p.i., with yields increasing until 12 h p.i. The transcripts remained stable until at least 48 hr. p.i. (FIG. 3A). The lef-2 transcripts were also analysed at selected times post infection using Northern blot hybridisation with a strand-specific riboprobe. FIG. 3B shows a typical result obtained with AcMNPV. A major transcript with a size of 1 kb appeared weakly at 5 hr p.i. and accumulated to a higher level up to 24 hr p.i. Other products including a band between 1.5 and 1.6 kb were detected both at early and late times after infection (FIG. 3B). Similar results were obtained with Aclef-2.c-myc5.

The transcription starts sites for lef-2 in AcMNPV-infected cells were determined by primer extension using two different oligonucleotides. Primer lef-2PE4 was used to detect the early start site. An extension product was obtained with mRNA extracted at 6 and 12 hr p.i., corresponding to a start site located 279 bp upstream from the lef-2 ATG codon. This mapped at a C within the sequence SEQ ID NO: 21 CAAT-GCGCCCGTTGT (FIG. 4A). When virus-infected cells were treated with cycloheximide, no products were obtained in the subsequent primer extension analysis, underlying the early character of this promoter. Primer lef-2PE3 was used to detect the late start site. One major extension product was obtained with mRNA extracted at 12 and 24 hr p.i. (FIG. 4B). This mapped the transcription start site at an adenine within a TAAG motif located 361 bp upstream of the ATG. When mRNA was extracted from virus-infected cells treated with aphidicolin, no primer extension products were obtained. Identical results were obtained with mRNA from Aclef-2.c-myc5'-infected cells (data not shown).

The 3' end of the lef-2 transcript was determined by sequencing DNA fragments generated by RACE-PCR after RT amplification of mRNA purified at 9 hr p.i. from AcMNPV- or Aclef-2.c-myc5'-infected cells. A single product with a length of approximately 330 bp was obtained from both samples (data not shown). Using the lef-2 RT1 primer, this fragment was sequenced to determine the precise point of addition of the poly(A) tail. This mapped at a A residue located 17 bp and 9 bp downstream from the stop codon of lef-2 and a AATAAA motif respectively. Combining the data from primer extension and 3' end mapping predicts an early lef-2 specific transcript of 928 bases and a late transcript of 1000 bases in AcMNPV-infected cells.

Expression of LEF-4, GP-64 and CHI in Aclef-2.c-myc5'-Infected Cells

To confirm that synthesis of a modified form of LEF-2 did not affect expression of other virus genes, the production of three other virus proteins was examined. These included an early gene (lef-4), a gene with both early and late transcription start sites (gp67) and a gene with only a late promoter (chiA). When production of these proteins was compared in Aclef-2.5'c-myc- or AcMNPV-infected cells, no differences in temporal synthesis or accumulation were observed (FIG. 5). It was interesting to note, however, that LEF-4 declined in abundance from about 12 h p.i.

Immunodetection of the C-MYC-tagged-LEF-2 in Infected Cells

Insect cells infected with Aclef-2.c-myc5' were examined using Western blot analysis in conjunction with the C-MYC-specific monoclonal antibody (9E10) to detect the tagged-LEF-2 (FIG. 6A). A specific product of approximately 25 KDa was detected in Aclef-2.c-myc5'-infected cells. The size of this product was consistent with the predicted combined molecular weights of LEF-2 (23.9 kDa; Ayres et al., 1994) and C-MYC (1.6 kDa). The protein was first detected weakly at 4 h p.i. and increased in abundance until 24 h.p.i., the last point tested. In AcMNPV-infected cells, the 25 kDa protein was not detected (FIG. 6B). In both experiments a major extra band, around 35 KDa, was detected even in the mock-infected lane. This corresponded to a cross reaction of our antibody against a host protein.

It was predicted that LEF-2 would be localised in the nuclei of virus-infected cells. It is associated with both DNA replication and late gene transcription. Both biochemical fractionation and immunofluorescence microscopy were used to test this hypothesis. Staining was found mainly in the nucleus of infected cells at both 9 and 24 hr p.i. The staining appeared to be concentrated in a central area that seemed to match the virogenic stroma. At early times after virus-infection (9 hr p.i.), the staining was observed as small discrete areas (foci) in the nucleus. Later in virus infection (24 hr p.i.) a large central area was stained. These results indicated that LEF-2 localised in the nucleus at both early and late times post infection.

Construction of a Recombinant Baculovirus with a Bacterial Origin of Replication A recombinant virus was constructed (Acp10Bac), which contained a bacterial origin of replication and chloramphenicol resistance gene inserted at the p10 locus within AcMNPV. This was amplified in Sf21 cells and used to isolate virus genomic DNA. The Acp10Bac DNA was used to transform DH10B cells via electroporation. Successful transformants were selected by growth on LB-agar plates containing chloramphenicol. Colonies of bacteria were amplified in liquid medium containing the same antibiotic and used to isolate virus genomic DNA. This DNA was used to transfect Sf21 cells. Three days after transfection cytopathic effects (cpe) were observed in the virus-infected cells. The virus-infected cell culture medium was harvested after seven days and the titre of the infectious virus determined using a plaque assay in Sf21 cells. The titre of the virus was $5 \times 10^7$ plaque forming units (pfu) per ml.

Construction of BacPAK6 with a Bacterial Origin of Replication

The construction of Acp10Bac demonstrated that it was feasible to insert a bacterial origin of replication into AcMNPV and produce a virus genome, which could be maintained as an episome in bacteria. The virus DNA could also be recovered from bacteria and used to transfect insect cells to reinitiate infection in the normal host. To make further manipulations of the baculovirus genome simpler, the polyhedrin gene within Acp10Bac was replaced with a copy of the beta-galactosidase gene (lacZ) from *E. coli*. This was achieved by cotransfecting insect cells with Acp10Bac DNA, derived from virus particles, with the transfer vector pBacPAK6 (Kitts and Possee, 1993). Recombination between the homologous sequences within the virus and plasmid resulted in the insertion of the lacZ into the polyhedrin locus of Acp10Bac to derive BacPAK6p10Bac. This virus was isolated by titration of the virus produced in the cotransfection by plaque assay in Sf21 cells. Virus plaques, which lacked polyhedra but stained blue in the presence of X-gal, were selected for further amplification in the same host cells. Genomic DNA was isolated from purified BacPAK6p10Bac virus particles and used to transform DH10B cells to confirm that the bacterial replication origin and antibiotic selection components were still functional.

Construction of a Recombinant Virus Lacking Genes Essential for Virus Replication BacPAK6p10Bac was modified to determine if removing a portion of the virus genome containing genes thought to be essential for virus replication prevented infection of insect cells. The region of the virus genome, which was chosen, was immediately downstream of the normal position of the polyhedrin gene (ca. 5050-12,000 base pairs; Ayres et al., 1994). This contains ORF1629, protein kinase 1 and lef-1, genes that are probably required for virus replication and several other putative genes of unknown function. To remove this region from the virus genome, an extra AvrII site was inserted within the 3' end of the ORF1629 coding region in the plasmid transfer vector pAcAL1 (King and Possee, 1992). This modification (FIG. 7); resulted in a conservative amino acid change within the predicted polypeptide sequence of ORF1629. The modified transfer vector pAcAL1-AvrII, mixed with BacPAK6p10Bac genomic DNA, which had been linearised with Bsu36I and used to cotransfect Sf21 cells. The progeny virus was titrated in a plaque assay and plaques that remained white in the presence of X-gal were isolated (AL1A-vrII). These were amplified in insect cells to provide working virus stocks, which were then used to derive virus genomic DNA. The virus genomic DNA was digested with AvrII and analysed using agarose gel electrophoresis. This showed that a 6385 bp fragment was excised from the virus genome after digestion with the restriction enzyme, as a consequence of DNA cleavage with AvrII within the ORF1629 and a native AvrII site within egt.

Religation of the AvrII-digested AL1AvrII and subsequent transfection of Sf21 cells failed to generate a virus that lacked the 6385 bp fragment generated by digestion with AvrII; only parental, undigested AL1AvrII was able to replicate. However, because replication of virus DNA in bacterial cells did not depend on these sequences, it was possible to transform DH10B with AvrII-digested, religated DNA to generate chloramphenicol-resistance colonies on appropriate agar selection plates. DNA isolated from amplified colonies could not initiate infection when it was used to transfect Sf21 cells. However, when it was mixed with pAcBglII-C, a plasmid containing a region of the AcMNPV genome overlapping the portion deleted from AL1AvrII, a productive infection was established in these cells. This was consistent with rescue of the defective form of AL1AvrII by recombination with the homologous regions in pAcBglII-C, thus replacing the virus genes that had been removed.

These results demonstrated that a defective form of AcMNPV DNA could be maintained in a bacterial system, purified and used to regenerate infectious virus by cotransfection with a rescuing plasmid. If the rescue plasmid contained a foreign gene, it would be an ideal way to make a recombinant virus for heterologous protein production. The plasmid used for the rescue experiment was pAcBglII-C, which is 15150 bp. This is too large to use as a transfer vector for carrying foreign genes. Most baculovirus transfer vectors used to insert foreign genes into the virus genome are smaller (5.0-10.0 kbp) and unsuitable for the rescue of the deletion within AL1AvrII. It was necessary, therefore, to construct a defective baculovirus genome, maintained in bacterial cells, with a smaller deletion that could be rescued by available plasmid transfer vectors.

Construction of a Recombinant Virus Lacking Part of ORF1629

The ORF1629 encodes a protein, which forms part of the virus nucleocapsid (Vialard and Richardson, 1993). Earlier work (Possee et al., 1991) showed that it probably could not be removed from the virus genome. This hypothesis was tested by constructing BacPAK6, which contained three Bsu36I sites, so permitting the removal of part of the ORF1629 coding region (Kitts and Possee, 1993). When BacPAK6 was digested with Bsu36I, infectious virus could only be obtained if the linear virus DNA was mixed with a plasmid transfer vector prior to cotransfection of insect cells. The transfer vector restored ORF1629 function and facilitated virus replication. This is the principle of making recombinant viruses using linearised virus DNA. If the defective form of the virus DNA could be amplified in a heterologous system it would enable recombinant virus production without parental virus contamination.

The recombinant virus, BacPAK6p10Bac, which contains the bacterial origin of replication and chloramphenicol resistance gene, was digested with Bsu36I to remove part of ORF603, lacZ and the 3' coding region of ORF1629. The restriction enzyme left asymmetric ends, which were incompatible for subsequent ligation. Consequently, the DNA ends were repaired with the large sub-unit of the E. coli DNA polymerase 1 (Klenow) prior to ligation to create a circular molecule, lacking ORF603, lacZ and part of ORF1629. The ligation mixtures were used to transform E. coli DH10B cells and derive chloramphenicol-resistant colonies on agar plates. These were designated AcORF1629-3'−. Colonies were isolated, amplified in liquid cultures and virus DNA purified. When this DNA was used to transfect Sf21 cells in the absence of a rescuing plasmid, virus replication was not detected. However, when a baculovirus plasmid transfer vector, containing a copy of the lacZ coding region under the control of the polyhedrin gene promoter, was mixed with AcORF1629-3'− DNA prior to cotransfection of insect cells, a cpe was observed at 4 days p.i. When X-gal was added to the virus-infected cells, they turned blue after overnight incubation at 28° C. The progeny virus was harvested at 7 days p.i. and titrated in a plaque assay. When these plaques were stained with X-gal at 4 days p.i., all of them were blue. This indicated that every virus recombinant produced after cotransfection of insect cells with AcORF1629-3'−1 and a plasmid transfer vector contained a foreign gene.

Discussion

In this study, we used S. cerevisiae as a host to maintain the AcMNPV genome and permit the manipulation of lef-2, a gene that is essential for replication of the virus in insect cells (Passarelli and Miller, 1993). The method was adapted from a protocol developed for the production of recombinant viruses containing foreign genes, that eliminated the need for plaque purification (Patel et al., 1992). We retained the AUC elements, inserted in lieu of the AcMNPV polyhedrin gene, to facilitate DNA replication in yeast cells. Part of the lef-2 coding region was replaced with sup4-o within a transfer vector. This plasmid was then introduced into yeast cells harbouring the AcMNPV genome to effect the modification of lef-2 via homologous recombination. Although lef-2 was targeted in this study, the method could be readily adapted to modify any baculovirus gene. It should circumvent the difficulties frequently encountered when trying to inactivate virus-coding regions by insertion of a reporter gene such as lacZ after cotransfection of insect cells with virus DNA and a transfer vector. If the target sequence is essential for virus replication, recombinant viruses are unstable and rapidly lost from the population. This problem was encountered when trying to modify the AcMNPV ORF1629 (Possee et al., 1991), which encodes a nucleocapsid-associated protein (Vialard and Richardson, 1993). The failure to isolate a recombinant virus was indicative, but not satisfactory evidence that this gene cannot be deleted from the virus genome.

The product of lef-2 (Passarelli and Miller, 1993) has a key role in viral replication. It was originally shown to be required for DNA replication (Kool et al., 1994; 1995; Lu and Miller, 1995; Lu et al., 1997). This conclusion derived from experiments where the transient replication of a reporter plasmid in the presence or absence of a number of baculovirus genes was measured. Although a very powerful system, its design precludes the identification of other roles for these genes in events subsequent to DNA replication. In other studies it was suggested that LEF-2 could also be involved directly in the regulation of very late gene expression, via the use of a virus with a mutation within the gene (Merrington et al., 1996) or anti-sense inhibition of its transcription (Sriram and Gopinathan, 1998). Clearly, there is scope for alternative approaches to studying the functions of this protein.

The recombinant virus DNA (AcΔ.lef-2.sup4-o) from yeast, with a deletion in lef-2, was unable to transfect Sf21 cells. This provided unambiguous evidence that lef-2 is required for propagation of the virus in insect cells. However, co-transfection of this DNA with a plasmid containing an unmodified copy of lef-2 permitted the recovery of infectious virus. This showed that no other mutation within the AcΔ.lef-2.sup4-o genome was responsible for the failure of the virus to replicate in insect cells. In future studies, it should be possible to co-transfect insect cells with AcΔ.lef-2.sup4-o DNA and plasmids containing selected modifications to lef-2. This would enable the function of each domain of the protein to be dissected in vivo, as judged by the failure or otherwise to regenerate an infectious virus. Incorporating a suitable reporter gene under early or late promoters into the system would also allow direct measurements of virus gene expression at different times after infection.

Some technical problems were noted during the use of the yeast system. Viral DNA extracted from yeast was not very efficient at establishing an infection when used to transfect Sf21 cells. Once the primary infection was established, however, virus stocks of normal titre could be obtained after subsequent passage in the same cells. This is probably due to the procedure used to extract the DNA from the yeast cells. The method is protracted and employs phenol extraction and ethanol precipitation to purify total DNA from the cells. It has previously been noted that precipitation of viral DNA reduces infectivity, due to the inevitable shearing that results on resuspension (King and Possee, 1992). The low infectivity of the viral DNA from yeast may, therefore, be due to only a sub-population of the DNA remaining as intact circles.

A low number of yeast colonies were obtained on transformation of the strain carrying the intact AcMNPV genome with the transfer vector containing the sup4-o gene. This may have been due to either a low recombination frequency or the action of the sup4-o gene product itself. When the yeast cells were transformed with the sup4-o-containing transfer vector, recombination was required to permit insertion of the sup4-o gene in place of lef-2. The efficiency of this recombination has not been estimated in yeast cells. It has been noted that, in insect cells, recombination occurs at a frequency of between 0.1 and 1%. A low frequency of recombination would lead to the production of only a few sup4-o+ colonies. Alternatively, the sup4-o gene encodes an ochre-suppressing tRNA. The ochre suppression may be a more stringent selection than an auxotrophic marker. We are currently investigating the use of alternative markers as insertable elements.

It was found that nine out of the twelve sup4-o-containing colonies produced virus DNA that was able to infect insect cells irrespective of the presence of the rescuing plasmid. This may have been due to the sup4-o gene inserting at alternate loci in the viral genome, causing no effect on virus replication. The sup4-o gene may also have inserted into the yeast chromosome itself, as it is known that only very short sequences are required for homologous recombination in yeast. We are currently working to improve the number of positive recombinants obtained.

We also used AcΔ.lef-2.sup4-o DNA as an intermediate step in the construction of a virus with an antigenic tag at the extremities of the protein. Tags are short polypeptide sequences for which we possess powerful monoclonal antibodies that facilitate identification and purification of the protein, even if it is present in low levels in the cells. In this example, the tagging procedure was successful only at the N terminal of LEF-2, suggesting that the C-terminal end is a critical position for the function of the protein. Recently, the Asp residue (D178) in the C-terminal of the protein was associated with the regulation of very late gene expression (Merrington et al., 1996). In addition, it has been noticed that the C-terminal domain is a cysteine rich area that presents structural homology with proteins, such as Adenovirus p300/CBP, involved in gene regulation (Eckner et al., 1994). Therefore it seems likely that modification of the C terminal end of LEF-2 cannot be tolerated because of a crucial role in its function.

Gene expression was compared in cells infected with AcMNPV or Aclef-2c-myc5', to determine if the addition of the tag to LEF-2 had any effect on transcription. Transcription analysis of lef-2 in AcMNPV and Aclef-2c-myc5'-infected cells showed no differences between the two viruses. In both viruses, a dual promoter included within the 350 nucleotides upstream of the ATG drove the expression of lef-2. The lef-2 transcripts were detected as early as 1 hr p.i. and reached a high level by 48 hr p.i. The early start site was mapped at a C within the sequence SEQ ID NO: 21 CAATGCG CCCGTTGT localised 279 nt upstream of the lef-2 ATG. A TATA-like sequence was evident between 35 and 30 nucleotides upstream from the transcription initiation site, confirming the cellular structure of this promoter. The late start site was mapped within the characteristic sequence TAAG located 361 nucleotides upstream of the start codon. Similar sites were recently found for the closely related BmNPV lef-2 (Sriram and Gopinathan, 1998). Identifying the polyadenylation anchor site 17 nucleotides downstream from the lef-2 translation stop codon completed the transcriptional analysis. The production of LEF-4, GP64 and chitinase was studied to determine that the addition of the C-MYC tag to LEF-2 did not have subtle effects on early and late virus gene expression. We concluded that the modification to lef-2 was neutral with respect to virus replication.

Using an antibody against the C-MYC epitope, the kinetics of LEF-2 production was analysed. The protein, with an expected size of 25 kDa, was first detected four hours after infection. Its quantity increased during the late phase of the infection. This result was in agreement with the RNA concentration during the viral cycle. However, the level of expression was found to be quite low even though a late promoter was involved in the transcription of the lef-2. Recent data suggested the importance of the sequence directly upstream from the TAAG motif for the selection and the level of expression of a late promoter (Mans and Knebel-Mörsdorf, 1998). Reduced helix stability was found to correlate with functional TAAG motifs. In the case of the lef-2 late promoter, the upstream sequence was sufficiently A/T-rich to create a functional late promoter but not high enough to derive a strong late promoter. This observation may explain the results obtained for the LEF-2 production. Due to the low level of lef-2 expression, the detection of the protein by a classic indirect immuno-fluorescence was impossible with our anti-c-myc antibody. We improved the sensitivity of detection using an amplification method which consisted of incubating fixed cells twice with primary and secondary antibodies. We observed a nuclear localisation of LEF-2 at both early and late times post infection. This was consistent with roles for the protein in both DNA replication and late virus gene expression. Others antibodies obtained against the complete LEF-2 over produced in bacteria or against synthetic peptides failed to detect efficiently the protein in both western blot and indirect immunofluorescence microscopy, revealing the poor antigenic character of the protein. These results, or lack of them, validate the approach of using a well-defined epitope and appropriate antibody for the detection of such proteins. The method should be applicable to any protein that is expressed at a low level in baculovirus-infected cells and presents difficulties in raising an antiserum.

The insertion of a bacterial origin of replication and chloramphenicol resistance gene at the p10 locus in AcMNPV (Acp10Bac) enabled virus DNA amplification within bacteria Virus DNA recovered from these bacteria was able to transfect insect cells and regenerate infectious virus progeny. These results were consistent with the observations made by Luckow et al (993), that baculovirus genomes could be maintained in *E. coli*. Their experiments were based on earlier studies, which showed that 300 kbp bacterial artificial chromosomes (Bacs) could be maintained in *E. coli* (REF). The propagation of such large DNA molecules in bacterial cells has been essential for the rapid progress made in the sequencing of the complete human genome and other species.

We extended our results further by constructing a baculovirus mutant (AL1AvrII) lacking at least three genes (ORF1629, protein kinase 1 and lef-1) thought to be required for replication in insect cells. This virus genome was maintained in bacterial cells since it was incapable of replication in Sf21 cells, as demonstrated after transfection of these cells with AL1AvrII DNA. However, when the virus DNA was mixed with pAcBglII-C, which spans the region missing from AL1AvrII, prior to cotransfection of insect cells, infectious virus was recovered and amplified to normal titres.

These results demonstrated the principle of our invention, that non-infectious baculovirus DNA could be rescued by cotransfection with a suitable plasmid. They were extended by constructing another AcMNPV mutant (AcORF1629-3'), which lacked only a small region of the 3' coding region of ORF1629. This virus DNA could be mixed with a baculovirus transfer vectors used to make recombinant viruses and cotransfected into insect cells to make infectious virus. We used a rescuing plasmid (pBacPAK6) which contained a copy of the lacZ gene under the control of the polyhedrin gene promoter, but any similar vector could be used. The advantage of our system is that most baculovirus transfer vectors, compatible with the polyhedrin gene locus, can be used to make recombinant virus.

The major feature of our system is that there is no contamination of the recombinant virus preparation with parental virus. This means that plaque assays subsequent to the original transfection do not have to be performed. Our new method for making recombinant baculoviruses is compared with the Bac-to-Bac and linear DNA methods currently widely used by research laboratories and Pharmaceutical-companies. It offers a saving in time of several days over both methods and significantly decreases the number of manipulations required to make a recombinant virus.

Both of the viruses (AL1AvrII and AcORF1629-3') made in this study had the bacterial replicon inserted at the p10 gene locus. Although this is not a problem, it does leave extra sequences in the recombinant virus after the DNA is rescued with a plasmid transfer vector in Sf21 cells. Therefore, we propose to make a second generation of viruses, which have to the bacterial replicon inserted at the polyhedrin gene locus. These viruses will also be unable to replicate in insect cells, because part of ORF1629 will be missing. They will represent an advance over the viruses made in this study, because the foreign gene from the rescuing transfer vector will replace the bacterial replicon as recombination takes place in insect cells.

We also anticipate that this new method could be adapted for use in 96-well (or greater) multi-well microtitre plates. The use of a robotic device to manipulate reagents would make it feasible to generate very large numbers of recombinant baculoviruses very quickly and without a large input of labour. It might be possible to coat the wells of such plates with the baculovirus DNA so that it could be resuspended prior to use by adding appropriate buffer containing the plasmid transfer vector, then adding lipofectin to mediate the formation of DNA-lipid complexes before adding insect cells to initiate cotransfection. This would form the basis of a very convenient kit for making recombinant baculoviruses.

The results show that it is possible to rescue replication-deficient virus using a rescue vector encoding a gene encoding a protein for restoring replication. The inventors have realised that it is possible to take this a step further by inserting a foreign gene into the rescue vector. The foreign gene may then be recombined with the baculovirus at the same time as the gene for restoring replication. Such a recombinatorial event can be selected for because the recombined virus containing the foreign gene will be able to replicate.

REFERENCES

Ahrens, C. H. & Rohrmann, G. F. (1995). Identification of essential trans-acting regions required for DNA replication of the *Orgyia pseudotsugata* baculovirus multinucleocapsid nuclear polyhedrosis virus: lef-1 is an essential replication gene. *Virology* 207, 417-428.

Ausubel, F. M., Brent, R., Kingston, R. E., Moore, D. D., Seidman, J. G., Smith, J. A. (Struhl, K. (1994). *Current Protocols in Molecular Biology*. Wiley, New-York.

Ayres, M. D. Howard, S. C., Kusio, J., López-Ferber, M. (Possee, R. D. (1994). The complete DNA sequence of *Autographa californica* nuclear polyhedrosis virus. *Virology* 202, 586-605.

Blissard, G. W. (Rohrmann, G. F. (1989). Location, sequence, transcriptional mapping, and temporal expression of the gp64 envelope glycoprotein gene of the *Orgyia pseudotsugata* multicapsid nuclear polyhedrosis virus. *Virology* 170, 537-555.

Durantel, D. Croizier, L., Ayres, M. D., Croizier, G., Possee, R. D. & López-Ferber, M. (1998a). The pnkl/pnl gene (ORF 86) of *Autographa californica* nucleopolyhedrovirus is a non essential, immediate early gene. *J. Gen. Virol.* 79, 629-637.

Durantel, D., Croizier, G., Ravallec, M. & López-Ferber, M. (1998b). Temporal expression of the AcMNPV lef-4 gene and subcellular localisation of the protein. *Virology* 241, 276-284.

Eckner, R. Ewen, M. E., Newsorme, D., Gerdes, M., Decaprio, J. K., Lawrence, J. B. & Linvington. D. M. (1994). Molecular cloning and functional analysis of the adenivirus associated 300 kD protein (p300) reveals a protein with properties of a transcription adaptor. *Genes Dev.* 8, 869-884.

Evan, G. I., Hancock, D. C., Littlewood, T. & Pauza, C. D. (1986). Characterization of the human c-myc protein using antibodies prepared against synthetic peptides. *Ciba Found Symp* 119, 245-263.

Evans, J. T., Leisy, D. J. & Rohrmann; G. F. (1997). Characterisation of the interaction between the baculovirus replication factors LEF-1 and LEF-2. *J. Virol.* 71, 3114-3119.

Fan, X., MacLachlin, J. R. & Weaver, R. F. (1998). Identification and characterisation of a protein kinase-interacting protein encoded by the *Autographa californica* Nuclear polyhedrosis virus. *Virology* 240, 175-182.

Fan, X., Thirunavukkarasu, K. & Weaver, R. F. (1996). Temperature-sensitive mutations in the protein kinase-1 (pk-1) gene of the *Autographa californica* nuclear polyhedrosis virus that block very late gene expression. *Virology* 224, 1-9.

Fitzgerald-Hayes, M. (1987). Yeast centromeres. *Yeast* 3, 187-200.

Funk, C. J., Harwood, S. H. & Rohrmann, G. F. (1998). Differential stability of baculovirus late transcription complexes during initiation and elongation. *Virology* 241, 131-140.

Gomi, S., Ecale Zhou, C., Yih, W., Majima, K. and Maeda, S. (1997). Deletion analysis of eighteen late expression factor gene homologues of the baculovirus BmNPV. *Virology* 230, 35-47.

Goodman, H. M., Olson, M. V. & Hall, B. D. (1977). Nucleotide sequence of a mutant eukariotic gene: the yeast tyrosine inserting ochre suppressor sup4-o. *Proc. Natl. Acad. Sci. U.S.A.* 74, 5453-5457.

Graham, F. L. and Vander Eb A. J. (1973). *Virol.* 52, 456.

Guarino, L. A., Xu, B., Jin, J. & Dong, W. (1998). A virus-encoded RNA polymerase purified from baculovirus infected cells. *J. Virol.* 72, 7985-7991.

Hawtin, R. E., Arnold, K., Ayres, M. D., Zanotto, P. M. A., Howard S. C., Gooday, G. W., Chappel, L. H., Kitts, P. A., King, L. A. & Possee, R. D. (1995). Identification and preliminary characterisation of a chitinase gene in the *Autographa californica* nuclear polyhedrosis virus genome. *Virology* 212, 673-685.

Ito, H., Fukuda, Y., Murata, K. & Kimura, A. (1983). Transformation of intact yeast cells treated with alkali cations. *J. Bacteriol.* 153, 163-168

King, L. A. & Possee, R. D. (1992). "The Baculovirus Expression System. A Laboratory Guide," first ed. Chapman and Hall, London.

Kitts, P. A. and Possee, R. D. (1993). A method for producing recombinant baculovirus expression vectors at high frequency. *Biotechniques* 14, 810-817.

Kool, M., Ahrens, C. H., Vlak, J. M. & Rohrmann, G. F. (1995). Replication of baculovirus DNA. *J. Gen. Virol.* 76, 2103-2118.

Kool, M., Ahrens, C., Goldbach, R. W., Rohrmann, G. F. & Vlak, J. M. (1994). Identification of genes involved in DNA replication of the *Autographa californica* baculovirus. *Proc. Natl. Acad. Sci. U.S.A.* 91, 11212-11216.

Laemmli, U. K. (1970). Cleavage of structural proteins during the assembly of the head of bacteriophage T4. *Nature* 227, 680-685.

Lu, A., Krell, P. J., Vlak, J. M. & Rohrmann, G. F. (1997). Baculovirus DNA replication. In: *The baculoviruses* (Miller, L. K., ed.) p. 171-192. Plenum press, New-York.

Lu, A. & Miller, L. K. (1995). The role of eighteen baculovirus late expression factor genes in transcription and DNA replication. *J. Virol.* 69, 975-982.

Lu, A. & Miller, L. K. (1994). Identification of three late expression factor genes within the 33.8- to 43.3-map unit region of *Autographa californica* nuclear polyhedrosis virus. *J. Virol.* 68, 6710-6718.

Lu, A. & Miller, L. K. (1997). Regulation of baculovirus late and very late gene expression. In: *The baculoviruses* (Miller, L. K., ed.) p. 193-216. Plenum press, New-York.

Luckow, V. A., Lee, S. C., Barry, G. F. and Olins, P. O. (1993). Efficient generation of infectious recombinant baculoviruses by site-specific transposon-mediated insertion of foreign genes into a baculovirus genome propagated in *Escherichia coli J. Virol.* 67, 4566-4579.

McLachlin, J. R., Yang, S. & Miller L. K. (1998). A baculovirus mutant defective in PKIP, a protein which interacts with a virus-encoded protein kinase. *Virology* 246, 379-391.

McLachlin, J. R. & Miller L. K. (1994). Identification and characterization of vlf-1, a baculovirus gene involved in very late gene expression. *J. Virol.* 68, 7746-7756.

Merrington, C. L., Kitts, P. A., King, L. A., and Possee, R. D. (1996). An *Autographa californica* nucleopolyhedrovirus lef-2 mutant: Consequences for DNA replication and very late gene expression. *Virology* 217, 338-348.

Newman, A. and Norman, C. (1991). Mutations in yeast U5 snRNA alter the specificity of 5' splice-site cleavage. *Cell* 65, 115-123.

Passarelli, A. L. & Miller, L. K. (1993a). Three baculovirus genes involved in late and very late gene expression: ie-1, ie-N, and lef-2. *J. Virol.* 67, 2149-2158.

Patel, D., Nasmyth, K. & Jones, N. (1992). A new method for the isolation of recombinant baculovirus. *Nucleic Acids Res* 20, 97-104.

Possee, R. D. (1986). Cell-surface expression of influenza virus haemagglutinin in insect cells using a baculovirus vector. *Virus Research* 5, 43-47.

Possee, R. D., Gearing, K. L., Howard, S. C, Ayres, M. D., Sun, T. -P. and Hill-Perkins. M. S. (1990). Nucleotide sequence of the *Autographa californica* Nuclear Polyhedrosis Virus 9.4 kbp EcoRI-I and —R (Polyhedrin Gene) Region. *Virology* 185, 229-241.

Proudfoot. N. (1991). Poly(A) signals. *Cell* 64, 671-674.

Rapp, J. C., Wilson, J. A. & Mileer, L. K. (1998). Nineteen baculovirus open reading frames, including lef-12 support late gene expression. *J. Virol.* 72, 10197-10206.

Ross, L. & Guarino, L. A. (1997). Cycloheximide inhibition of delayed early gene expression in baculovirus-infected cells. *Virology* 232, 105-113.

Sambrook, J., Fritsch, E. F. and Maniatis, T. (1989). "Molecular Cloning: A Laboratory Manual". Cold Spring Harbor Laboratory, Cold Spring Harbor, N.Y.

Schiestl, R. H. & Gietz, R. D. (1989). High efficiency transformation of intact yeast cells using single stranded nucleic acids as a carrier. *Curr. Genet.* 16, 339-346.

Sherman, F (1991). Getting started with yeast. *Methods. in Enzymol.* 194, 3-21.

Shizuya, H., Birren, B., Kim, U-J., Mancino, V., Slepak, T., Tachiiri, Y. and Simon, M. (1992). Cloning and stable maintenance of 300-kilobase pair fragments of human DNA in *Escherichia coli* using an F-factor-based vector. *Proc. Natl. Acad. Sci USA.* 89, 8794-8797.

Stinchcomb. D. T., Struhl, K. & Davis, R. W. (1979). Isolation and characterisation of a yeast chromosomal replicator. *Nature* 282, 39-43

Todd, J. W., Passarelli, L. A. & Miller, L. K. (1995). Eighteen baculovirus genes, including lef-11, p35, 39k, and p47, support late gene expression. *J. Virol.* 69, 968-974.

Todd, J. W., Passarelli, L. A. & Miller, L. K. (1996). Factors regulating baculovirus late and very late gene expression in transient-expression assays. *J. Virol.* 70, 2307-2317.

Vilard, J. E. and Richardson, C. D. (1993). The 1629-nucleotide open reading frame located downstream of the *Autographa californica* nuclear polyhedrosis virus polyhedrin gene encodes a nucleocapsid-associated phosphoprotein. *J. Virol.* 67, 5859-5866.

Weyer, U. and Possee, R. D. (1988). Functional analysis of the p10 gene 5' leader sequence of the *Autographa californica* nuclear polyhedrosis virus. *Nucleic Acids Research* 16, 3635-3653.

Weyer, U., Knight, S, and Possee, R. D. (1990). Analysis of very late gene expression by *Autographa californica* nuclear polyhedrosis virus and the further development of multiple expression vectors. *Journal of General Virology* 71, 1525-1534.

Wigler, M. et al. (1977) *Cell.* 11, 223.

Yang, S. & Miller, L. K. (1998a). Expression and mutational analysis of the baculovirus very late factor 1 (vlf-1) gene. *Virology* 245, 99-109.

Yang, S. & Miller, L. K. (1998b). Control of baculovirus polyhedrin gene expression by very late factor 1. *Virology* 248, 131-138.

The invention claimed is:

1. A method for cloning a gene comprising the steps of:
   (i) providing a naked circular replication-deficient baculovirus vector capable of being maintained in a bacterial cell;
   (ii) providing a rescue vector comprising (a) a nucleic acid sequence, which is capable of restoring replication to the replication-deficient baculovirus vector, and (b) at least one gene to be cloned; and
   (iii) permitting the circular replication-deficient baculovirus vector and the rescue vector to recombine in an insect cell to produce a replication-enabled baculovirus vector comprising the at least one gene to be cloned.

2. A method according to claim 1, wherein the replication-deficient baculovirus vector lacks a functional gene necessary for viral replication and the rescue vector comprises a gene necessary for restoring the functional gene.

3. A method according to claim 2, wherein the functional gene is selected from lef-1, lef-2, lef-3, lef-4, lef-5, lef-6, lef-7, lef-8, lef-9, lef-10, lef-11, lef-12, dnapol, p143, ie-1, ie-2, p47, ORF1629 and pp31.

4. A method according to claim 3, wherein the functional gene is lef-2.

* * * * *

```
                         SEQUENCE LISTING

<160> NUMBER OF SEQ ID NOS: 26

<210> SEQ ID NO 1
<211> LENGTH: 58
<212> TYPE: DNA
<213> ORGANISM: Baculovirus

<400> SEQUENCE: 1
gatccataat ggagcaaaag ctcatttctg aagaggactt gaattctaga taactgca        58

<210> SEQ ID NO 2
<211> LENGTH: 50
<212> TYPE: DNA
<213> ORGANISM: Baculovirus

<400> SEQUENCE: 2
gttatctaga attcaagtcc tcttcagaaa tgagcttttg ctccattatg                 50

<210> SEQ ID NO 3
<211> LENGTH: 25
<212> TYPE: DNA
<213> ORGANISM: Baculovirus

<400> SEQUENCE: 3
cggcagatct ataatggcga atgca                                            25

<210> SEQ ID NO 4
<211> LENGTH: 31
<212> TYPE: DNA
<213> ORGANISM: Baculovirus

<400> SEQUENCE: 4
gccaggatcc ataattacaa ataggattga g                                     31

<210> SEQ ID NO 5
<211> LENGTH: 24
<212> TYPE: DNA
<213> ORGANISM: Baculovirus

<400> SEQUENCE: 5
cggctctaga atggcgaatg catc                                             24

<210> SEQ ID NO 6
<211> LENGTH: 28
<212> TYPE: DNA
<213> ORGANISM: Baculovirus

<400> SEQUENCE: 6
gccgctgcag tcaataatta caaatagg                                         28
```

```
<210> SEQ ID NO 7
<211> LENGTH: 24
<212> TYPE: DNA
<213> ORGANISM: Baculovirus

<400> SEQUENCE: 7
ggccggtacc gagttcgttg acgc                                          24

<210> SEQ ID NO 8
<211> LENGTH: 30
<212> TYPE: DNA
<213> ORGANISM: Baculovirus

<400> SEQUENCE: 8
cgcgagatct acttcgcggc ttctcgcacc                                    30

<210> SEQ ID NO 9
<211> LENGTH: 30
<212> TYPE: DNA
<213> ORGANISM: Baculovirus

<400> SEQUENCE: 9
ggccctgcag ataataaaac aattataaat                                    30

<210> SEQ ID NO 10
<211> LENGTH: 24
<212> TYPE: DNA
<213> ORGANISM: Baculovirus

<400> SEQUENCE: 10
cgcgaagctt agcaactata tatt                                          24

<210> SEQ ID NO 11
<211> LENGTH: 30
<212> TYPE: DNA
<213> ORGANISM: Baculovirus

<400> SEQUENCE: 11
aagctcgtgc cggaacgcgt gcacagatcg                                    30

<210> SEQ ID NO 12
<211> LENGTH: 31
<212> TYPE: DNA
<213> ORGANISM: Baculovirus

<400> SEQUENCE: 12
tgtagtcggc agttcatttt gggcgtgatc g                                  31

<210> SEQ ID NO 13
<211> LENGTH: 25
<212> TYPE: DNA
<213> ORGANISM: Baculovirus

<400> SEQUENCE: 13
aagaaaacaa tgtaccgcgc ggcgg                                         25

<210> SEQ ID NO 14
<211> LENGTH: 32
<212> TYPE: DNA
<213> ORGANISM: Baculovirus

<400> SEQUENCE: 14
atgcgaattc tcaataatta caaataggat tg                                 32
```

```
<210> SEQ ID NO 15
<211> LENGTH: 33
<212> TYPE: DNA
<213> ORGANISM: Baculovirus

<400> SEQUENCE: 15
aaattcagat ataaagacgc tgaaaatcat ttg                                    33

<210> SEQ ID NO 16
<211> LENGTH: 29
<212> TYPE: DNA
<213> ORGANISM: Baculovirus

<400> SEQUENCE: 16
tgattttcag cgtctttata tctgaattt                                         29

<210> SEQ ID NO 17
<211> LENGTH: 34
<212> TYPE: DNA
<213> ORGANISM: Baculovirus

<400> SEQUENCE: 17
attttcgctc taacatacca ccctagggat gtac                                   34

<210> SEQ ID NO 18
<211> LENGTH: 38
<212> TYPE: DNA
<213> ORGANISM: Baculovirus

<400> SEQUENCE: 18
gtacatccct agggtggtat gttagagcga aaatcaaa                               38

<210> SEQ ID NO 19
<211> LENGTH: 35
<212> TYPE: DNA
<213> ORGANISM: Baculovirus

<400> SEQUENCE: 19
ctagggatta taaatttaat gaattattaa aatac                                  35

<210> SEQ ID NO 20
<211> LENGTH: 31
<212> TYPE: DNA
<213> ORGANISM: Baculovirus

<400> SEQUENCE: 20
gtattttaat aattcattaa atttataatc c                                      31

<210> SEQ ID NO 21
<211> LENGTH: 15
<212> TYPE: DNA
<213> ORGANISM: Baculovirus

<400> SEQUENCE: 21
caatgcgccc gttgt                                                        15

<210> SEQ ID NO 22
<211> LENGTH: 19
<212> TYPE: PRT
<213> ORGANISM: Baculovirus

<400> SEQUENCE: 22

Met Glu Gln Lys Leu Ile Ser Glu Glu Asp Leu Asn Ser Arg Met Ala
```

```
                            -continued
1              5             10            15

Asn Ala Ser

<210> SEQ ID NO 23
<211> LENGTH: 82
<212> TYPE: DNA
<213> ORGANISM: Baculovirus

<400> SEQUENCE: 23
gccgcgaagt agatctggat ccataatgga gcaaaagctc atttctgaag aggacttgaa    60
ttctagaatg gcgaatgcat cg                                             82

<210> SEQ ID NO 24
<211> LENGTH: 24
<212> TYPE: PRT
<213> ORGANISM: Baculovirus

<400> SEQUENCE: 24

Leu Asn Pro Ile Cys Asn Tyr Gly Ser Ile Met Glu Gln Lys Leu Ile
1              5                   10                  15

Ser Glu Glu Asp Leu Asn Ser Arg
            20

<210> SEQ ID NO 25
<211> LENGTH: 82
<212> TYPE: DNA
<213> ORGANISM: Baculovirus

<400> SEQUENCE: 25
ctcaatccta tttgtaatta tggatccata atggagcaaa agctcatttc tgaagaggac    60
ttgaattcta gataactgca ga                                             82

<210> SEQ ID NO 26
<211> LENGTH: 13
<212> TYPE: PRT
<213> ORGANISM: Artificial Sequence
<220> FEATURE:
<223> OTHER INFORMATION: C-MYC epitope

<400> SEQUENCE: 26

Met Glu Gln Lys Leu Ile Glu Glu Asp Leu Asn Ser Arg
1              5                   10
```